United States Patent
Rugel et al.

(10) Patent No.: US 11,423,335 B2
(45) Date of Patent: *Aug. 23, 2022

(54) DATA PROCESSING SYSTEM WITH MACHINE LEARNING ENGINE TO PROVIDE OUTPUT GENERATING FUNCTIONS

(71) Applicant: Allstate Insurance Company, Northbrook, IL (US)

(72) Inventors: John Rugel, Hawthorn Woods, IL (US); Brian Stricker, Northbrook, IL (US); Howard Hayes, Glencoe, IL (US); Surender Kumar, Palatine, IL (US); Matthew Olenak, Chicago, IL (US)

(73) Assignee: Allstate Insurance Company, Northbrook, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/087,953

(22) Filed: Nov. 3, 2020

(65) Prior Publication Data
US 2021/0073681 A1 Mar. 11, 2021

Related U.S. Application Data

(63) Continuation of application No. 16/382,561, filed on Apr. 12, 2019, now Pat. No. 10,839,319, which is a (Continued)

(51) Int. Cl.
*G06N 20/00* (2019.01)
*G06Q 30/02* (2012.01)
(Continued)

(52) U.S. Cl.
CPC .......... *G06N 20/00* (2019.01); *G06F 11/321* (2013.01); *G06F 11/3438* (2013.01);
(Continued)

(58) Field of Classification Search
CPC ..... G09B 7/02; G06F 11/261; G06F 17/5022; G06F 17/504
See application file for complete search history.

(56) References Cited

U.S. PATENT DOCUMENTS 5,544,649 A 8/1996 David et al.
5,918,222 A 6/1999 Fukui et al.
(Continued)

OTHER PUBLICATIONS

Dec. 28, 2017—(US) Non-Final Office Action—U.S. Appl. No. 15/727,226.
(Continued)

*Primary Examiner* — Elias Desta
(74) *Attorney, Agent, or Firm* — Polsinelli PC

(57) ABSTRACT

Methods, apparatuses, systems, and computer-readable media for identifying and executing one or more interactive condition evaluation tests and collecting and analyzing user behavior data to generate an output are provided. In some examples, user information may be received and one or more interactive condition evaluation tests may be identified. An instruction may be transmitted to a computing device of a user and executed on the computing device to enable functionality of one or more sensors that may be used in the identified tests. Upon initiating a test, data may be collected from the one or more sensors. The collected sensor data may be transmitted to the system and processed using one or more machine learning datasets. Additionally, user behavior data may be collected and processed using one or more machine learning datasets. The sensor data, the user behavior data, and other data may be used together to generate an output.

20 Claims, 18 Drawing Sheets

Related U.S. Application Data continuation-in-part of application No. 16/160,332, filed on Oct. 15, 2018, now Pat. No. 10,445,662, which is a continuation of application No. 15/727,226, filed on Oct. 6, 2017, now Pat. No. 10,140,199, which is a continuation of application No. 15/716,983, filed on Sep. 27, 2017, now abandoned.

(51) Int. Cl.

| | | |
|---|---|---|
| *G06F 11/32* | (2006.01) | |
| *G06Q 30/06* | (2012.01) | |
| *G06F 11/34* | (2006.01) | |
| *G16H 10/60* | (2018.01) | |
| *G06V 30/194* | (2022.01) | |

(52) U.S. Cl.
CPC ..... *G06Q 30/0271* (2013.01); *G06Q 30/0627* (2013.01); *G06V 30/194* (2022.01); *G16H 10/60* (2018.01)

(56) References Cited

U.S. PATENT DOCUMENTS

| | | | |
|---|---|---|---|
| 5,991,734 A * | 11/1999 | Moulson | G06Q 30/02 |
| | | | 358/447 |
| 6,077,304 A | 6/2000 | Kasuya | |
| 6,102,959 A | 8/2000 | Hardin et al. | |
| 6,487,704 B1 | 11/2002 | McNamara et al. | |
| 6,714,975 B1 * | 3/2004 | Aggarwal | G06Q 30/02 |
| | | | 709/224 |
| 6,829,753 B2 | 12/2004 | Lee et al. | |
| 7,130,783 B1 | 10/2006 | Harer et al. | |
| 7,490,085 B2 | 2/2009 | Walker et al. | |
| 8,422,994 B2 | 4/2013 | Rhoads | |
| 8,790,259 B2 | 7/2014 | Katra et al. | |
| 8,909,771 B2 | 12/2014 | Heath | |
| 9,111,455 B2 | 8/2015 | Rogers et al. | |
| 10,140,199 B1 | 11/2018 | Rugel et al. | |
| 10,445,662 B2 | 10/2019 | Rugel et al. | |
| 10,839,319 B2 | 11/2020 | Rugel et al. | |
| 10,878,344 B2 | 12/2020 | Rugel et al. | |
| 2006/0265260 A1 * | 11/2006 | Brown | G06Q 30/06 |
| | | | 705/26.64 |
| 2010/0083968 A1 | 4/2010 | Wondka et al. | |
| 2011/0301433 A1 | 12/2011 | Sadowsky et al. | |
| 2012/0240206 A1 | 9/2012 | Hoffman | |
| 2013/0346115 A1 | 12/2013 | Peak et al. | |
| 2015/0244850 A1 | 8/2015 | Rodriguez et al. | |
| 2016/0350274 A1 | 12/2016 | Deng et al. | |
| 2017/0018030 A1 | 1/2017 | Crouspeyre et al. | |
| 2017/0269586 A1 | 9/2017 | D'Andrea et al. | |
| 2019/0095815 A1 | 3/2019 | Rugel et al. | |

OTHER PUBLICATIONS

Jun. 1, 2018—(US) Final Office Action—U.S. Appl. No. 15/727,226.
Jul. 16, 2018—(US) Notice of Allowance—U.S. Appl. No. 15/727,226.
Dec. 14, 2018—(US) Non-Final Office Action—U.S. Appl. No. 16/160,332.
Dec. 26, 2018 (WO) International Search Report—App. PCT/US2018/52609.
Sep. 19, 2019—(US) Non-Final Office Action—U.S. Appl. No. 16/382,561.
Dec. 31, 2019 (US) Non-Final Office Action—U.S. Appl. No. 16/587,280.
Apr. 23, 2020—(US) Final Office Action—U.S. Appl. No. 16/382,561.
May 11, 2020—(WO) International Search Report & Written Opinion—PCT/US20/27395.
May 15, 2020—(US) Notice of Allowance—U.S. Appl. No. 16/587,280.
Jul. 13, 2020—(US) Notice of Allowance—U.S. Appl. No. 16/382,561.
Aug. 7, 2020—(US) Non-Final Office Action—U.S. Appl. No. 15/716,983.
Sep. 2, 2020—(US) Notice of Allowance—U.S. Appl. No. 16/587,280.
Jan. 25, 2021—(US) Non-Final Office Action—U.S. Appl. No. 16/189,374.
Apr. 20, 2021—(EP) Extended Search Report—App. No. 18863747.4.
May 13, 2021—(CA) Office Action—App 3076898.
May 3, 2021—(CA) Office Action—App. No. 3076898.
Feb. 11, 2021—(EP) Office Action—Application No. 168080984, 9 Pages.
Oct. 28, 2021—(US) Non-Final Office Action—U.S. Appl. No. 17/130,156, 6 Pages.

* cited by examiner

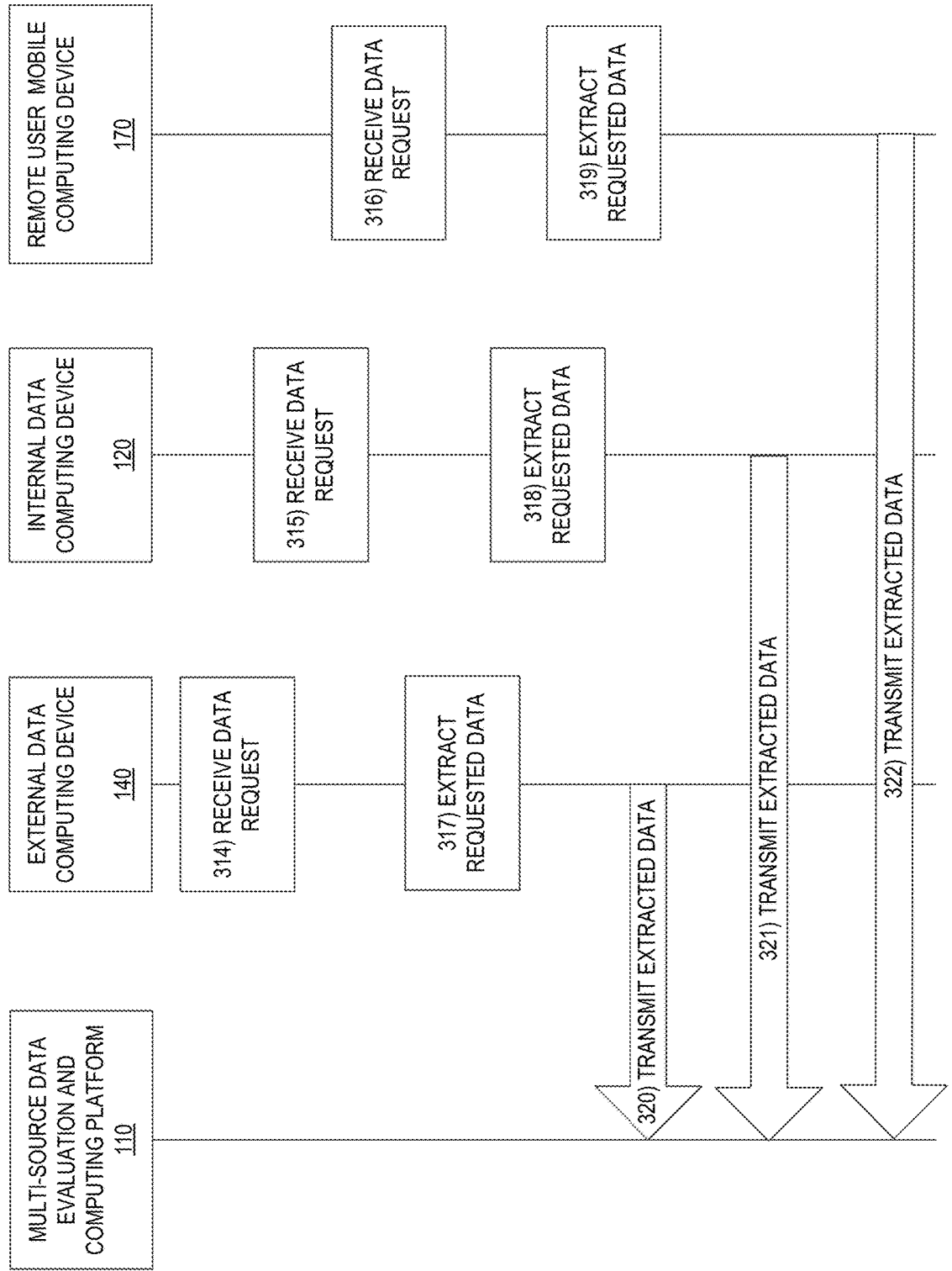

DATA PROCESSING SYSTEM WITH MACHINE LEARNING ENGINE TO PROVIDE OUTPUT GENERATING FUNCTIONS

CROSS REFERENCE TO RELATED APPLICATIONS

This application is a continuation of and claims priority to U.S. patent application Ser. No. 16/382,561, now U.S. Pat. No. 10,839,319, filed Apr. 12, 2019, and entitled "Data Processing System with Machine Learning Engine to Provide Output Generating Functions," which is a continuation-in-part of and claims priority to U.S. patent application Ser. No. 16/160,332, filed Oct. 15, 2018, and entitled "Data Processing System with Machine Learning Engine to Provide Output Generating Functions," which is a continuation of and claims priority to U.S. patent application Ser. No. 15/727,226, filed Oct. 6, 2017, and entitled "Data Processing System with Machine Learning Engine to Provide Output Generating Functions," which is a continuation of and claims priority to U.S. patent application Ser. No. 15/716,983, filed Sep. 27, 2017, and entitled "Data Processing System with Machine Learning Engine to Provide Output Generating Functions," all of which are incorporated herein by reference in their entirety.

TECHNICAL FIELD

Aspects of the disclosure generally relate to one or more computer systems, servers, and/or other devices including hardware and/or software. In particular, aspects are directed to executing interactive condition evaluation tests, collecting and analyzing user data, and using machine learning to generate an output. Further, it may be advantageous to collect and analyze behavior data related to the user from various data sources.

BACKGROUND

Mobile devices are being used to simplify people's lives around the world. However, it is often difficult to collect sufficient information via user input. In addition, determining an accuracy of information provided by a user can be difficult. Often, confirming accuracy may require in-person communication, additional documentation, and the like. Accordingly, executing a plurality of interactive tests generated by an entity to collect condition data, verify accuracy of data, and the like, may be advantageous.

SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Aspects of the disclosure relate to methods, computer-readable media, systems, and apparatuses for capturing and evaluating data related to a user to generate an output, such as an identification and/or determination of the user's eligibility and/or pricing for one or more products, services, incentives, discounts, etc.

In accordance with aspects of the disclosure, a system, computing device, or the like may capture and evaluate test data, user behavior data, and various other types of data. The data may be captured by or collected from one or more sources, such as user devices, sensors, remote computing devices, servers, databases, etc., with appropriate user permissions.

For example, test data may be captured when a user performs one or more interactive condition evaluation tests. User information may be received by the system, computing device, or the like. Based on the information, one or more interactive condition evaluation tests may be identified. An instruction, command, signal or the like, may be transmitted to a computing device of the user and executed on the computing device to enable functionality of one or more sensors that may be used in the identified interactive condition evaluation tests. In some examples, a user interface may be generated by the system, computing device, or the like. The user interface may include instructions for executing the identified interactive condition evaluation tests. Upon initiating an interactive condition evaluation test on the computing device, data may be collected from one or more sensors. A determination may be made as to whether a triggering event has occurred. If the triggering event has not occurred, data from the sensors may be continue to be collected. If the triggering event has occurred, the interactive condition evaluation test may be terminated and functionality associated with the sensors may be disabled. The data collected from the one or more sensors during the interactive condition evaluation test may be analyzed to determine test results, i.e., test data.

User behavior data may additionally be collected or captured with appropriate user permissions. User behavior data may be personal data collected by one or more devices associated with the user, from social media and/or email accounts associated with the user, etc. The user behavior data may additionally be collected by sources external to user, such as remote computing devices, servers, databases, etc.

Various other types of data may additionally be collected from one or more other sources (e.g., with appropriate user permissions).

The collected data, such as the test data, the user behavior data, and various other types of data, may be transmitted to the system, computing device, or the like, and may be analyzed and processed using one or more machine learning datasets to determine the user's health/wellness status, behavior, habits, lifestyle choices, etc. The system, computing device, or the like may use the processed data to calculate one or more user behavior scores related to the user and to generate a user behavior profile based on the user behavior scores. The user behavior scores and user behavior profile may be used alone or with other collected information to generate an output regarding the user's eligibility for one or more products, services, discounts, incentives, etc. and/or pricing related thereto. For instance, the user behavior score and user behavior profile may be used together with other collected information to determine an eligibility of the user, or pricing for the user, for a variable insurance product or service. The variable insurance product may be a behavior-based variable product, such as a life insurance, vehicle insurance, health insurance, etc. product. Pricing for the behavior-based variable product may comprise two components—a fixed pricing component and a variable pricing component. Pricing for the variable pricing component may vary or fluctuate over time based on the collected data. The generated output may further be transmitted to a computing device for display.

These and other features and advantages of the disclosure will be apparent from the additional description provided herein.

BRIEF DESCRIPTION OF THE DRAWINGS

A more complete understanding of the present disclosure and the advantages thereof may be acquired by referring to the following description in consideration of the accompanying drawings, in which like reference numbers indicate like features, and wherein:

FIGS. 3A-3I depict an illustrative event sequence for performing multi-source data evaluation and control functions, according to one or more aspects described herein.

DETAILED DESCRIPTION

Figure 1A:
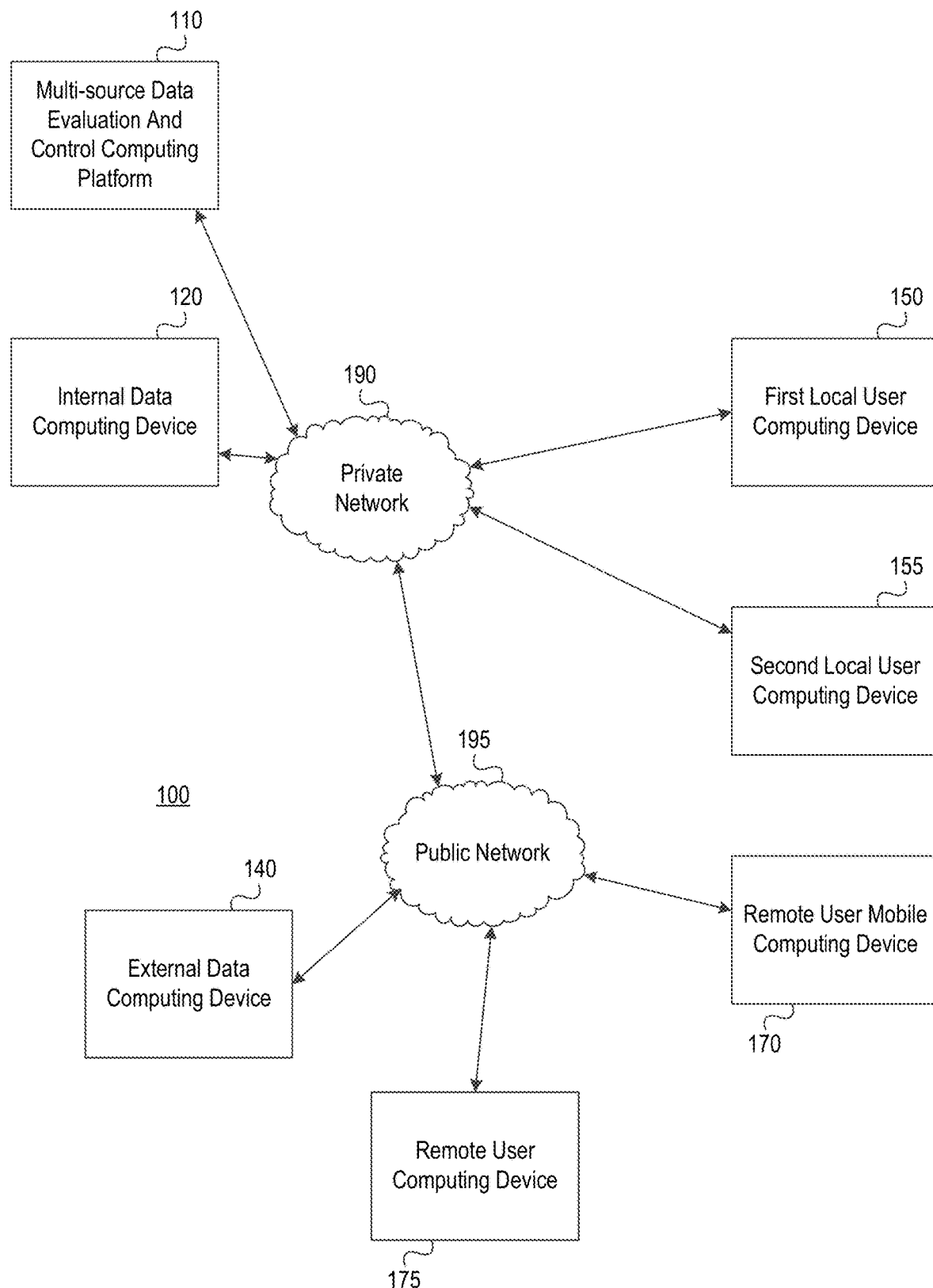
FIGS. 1A and 1B illustrate an illustrative computing environment for implementing multi-source data evaluation and control functions, according to one or more aspects described herein.

In the following description of the various embodiments, reference is made to the accompanying drawings, which form a part hereof, and in which is shown by way of illustration, various embodiments of the disclosure that may be practiced. It is to be understood that other embodiments may be utilized.

Mobile devices are being used to perform functions that, at one time, required interaction between users, such as a customer and a vendor, service provider, or the like. However, the accuracy of information provided by a user, the identity of a user providing input via the mobile device, and the like, may be difficult to confirm. Accordingly, it may be advantageous to use various forms of electronic data related to a user, and collected by one or more devices associated with the user and/or by other devices and sources, to determine the user's eligibility and pricing for one or more products, services, or the like. For example, it may be advantageous to use test data and user behavior data collected from a user's mobile device (or from other devices and sources) alone or together with other information to make such a determination. The test data may be collected in response to identifying and executing one or more interactive condition evaluation tests on the mobile device to evaluate a condition of a user. The user behavior data may be collected, with appropriate user permissions, from the user's mobile device, fitness or other wearable device, social media networks, email accounts, and the like. Various other types of data may be collected, with appropriate user permissions, from one or more other devices or sources, such as data from electronic health records, from third party or public databases, etc. The test data, the user behavior data, and the various other types of data may be processed and analyzed to make an assessment regarding the user's health/wellness status, social behavior, habits, lifestyle choices, etc. Based on the analysis, one or more user behavior scores related to the user may be calculated, and a user behavior profile, based on the user behavior scores, may be generated. The user behavior scores and user behavior profile may be used alone or with other collected information to determine a user's eligibility for one or more products or services, and/or to determine at least a component of pricing for a behavior-based variable product, and the like. The user's eligibility for the product or service or for the pricing or adjustment thereof may be determined periodically throughout ownership of the product or service.

In some examples, a user may request a product or service (e.g., via a mobile device). The request may be transmitted to a system, computing platform, or the like, which may process the request and transmit, to the mobile device, a request for additional information. The user may provide the requested additional information via the mobile device. The additional information may include information such as name, age, gender, height, weight, location, email address, social media account information, other account information, authorization to collect information from one or more devices associated with the user or one or more accounts associated with the user, and the like. Based on the information provided, one or more products or services for which the user may be eligible may be identified. For example, based on the information provided, the system may identify one or more behavior-based variable products, such as a life insurance product. In other examples, a user may currently have an existing product or service, which is identified using the requested additional information. The existing product or service may be, for example, a behavior-based variable insurance product.

The behavior-based variable product may be comprised of two pricing components—a variable pricing component and a fixed pricing component. The variable pricing component may be a component whose pricing may fluctuate based on a user's behavior as it relates to their health, wellness, and risk level as determined by various data collected about the user. That is data such as test data, user behavior data, and various other types of data may be collected on regular basis throughout the user's ownership of the product. The variable pricing component of the product may be adjusted periodically (e.g., daily, weekly, monthly, on a predetermined schedule, accordingly to a user request, etc.) based on the collected data. For example, the variable pricing component may be adjusted if the risk level determined based on user behavior data meets a first threshold value. The fixed pricing component may be a component whose pricing may not be affected by the user's behavior. The fixed pricing component may be based on an assessment of the user's health/wellness and risk level at the time the insurance product is purchased.

The fixed component may fluctuate for traditional market reasons outside of the user's control.

Based on the identified or the existing one or more products or services, one or more interactive condition evaluation tests may be identified to evaluate a health or wellness condition of the user. In some examples, the system may transmit an instruction to the mobile device to enable one or more sensors associated with the identified one or more interactive condition evaluation tests. The one or more tests may then be executed by the mobile device. Data from the one or more sensors may be collected during execution of the tests and may be transmitted to the system for processing.

The system may additionally collect user behavior data from the user's mobile device or other devices, social media networks, email accounts, etc., with appropriate user permissions. The system may also collect various other types of data from various other devices and electronic sources.

The system may use a machine learning engine and datasets to analyze and process the test data, the user behavior data, and the various other types of data to assess the user's health/wellness status, social behavior, habits, lifestyle choices, etc. A user behavior score and profile may be generated based on the assessment. The user behavior score and/or profile may be used together with other information to evaluate eligibility of the user for one or more products or services, determine pricing for one or more products or services or components of thereof, and to generate an output for a user (e.g., a product or service to offer), and the like.

These and other aspects will be described more fully herein.

Figure 1B:
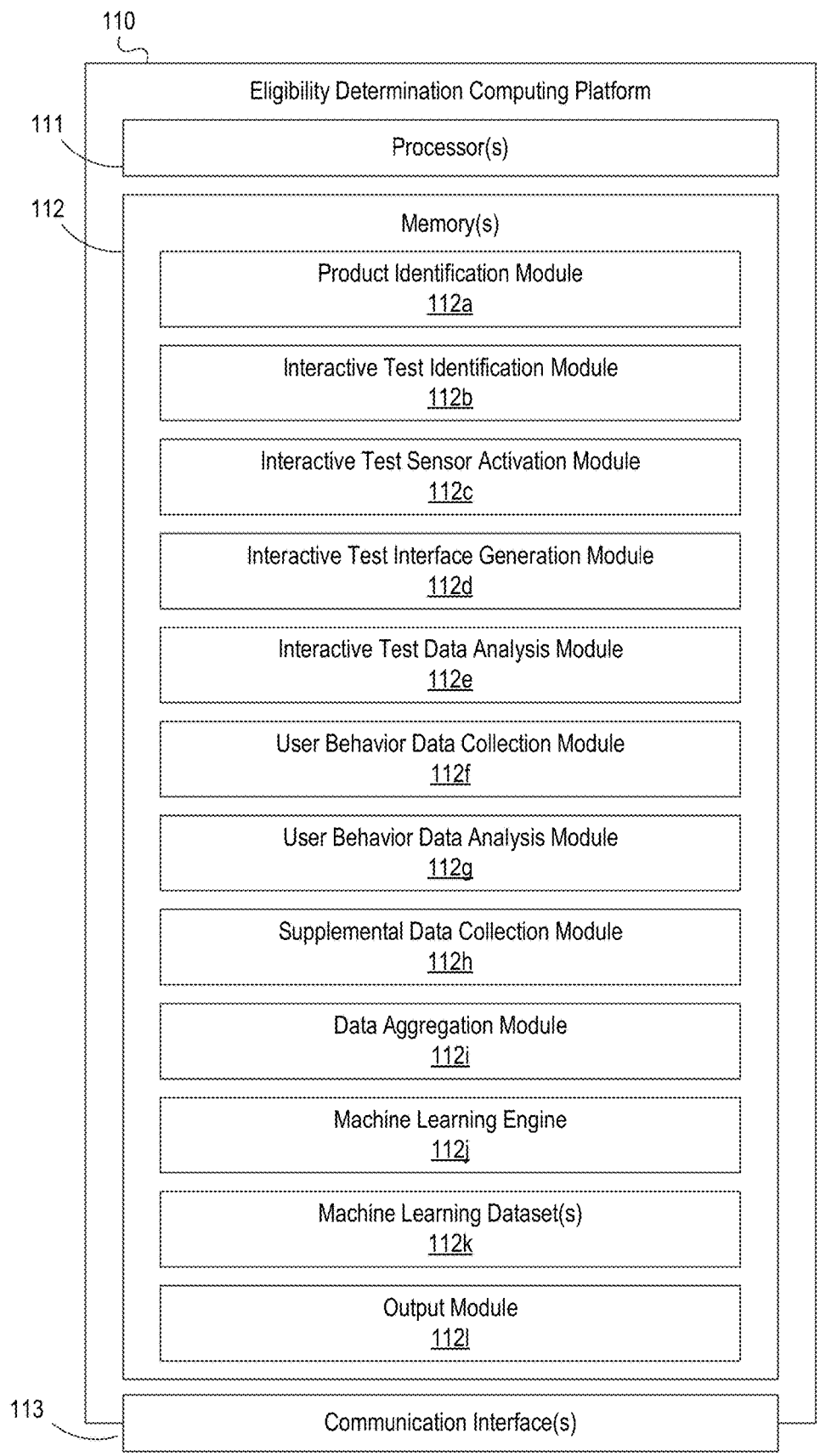

FIGS. 1A-1B depict an illustrative computing environment for implementing and using a multi-source data evaluation and control system in accordance with one or more aspects described herein.

Referring to FIG. 1A, computing environment 100 may include one or more computing devices and/or other computing systems. For example, computing environment 100 may include a multi-source data evaluation and control computing platform 110, an internal data computing device 120, a first local user computing device 150, a second local user computing device 155, an external data computing device 140, a remote user mobile computing device 170, and a remote user computing device 175.

The multi-source data evaluation and control computing platform 110 may be configured to host and/or execute one or more modules including instructions for providing various interactive condition evaluation test functions and/or factor prediction functions, one or more modules including instructions for performing various data collection and analysis functions. In some examples, the multi-source data evaluation and control computing platform 110 may be configured to generate, and initiate one or more interactive condition evaluation tests, receive data from a plurality of disparate sources (including data resulting from execution of the interactive condition evaluation tests, user behavior data, and various other types data), aggregate the data, use a machine learning engine to generate one or more predictions or assessments based on the data, and generate an output, such as a user's eligibility or pricing for a product or service.

One or more aspects described herein may be performed by one or more applications downloaded or otherwise provided to a computing device (such as the first local user computing device 150, the second local user computing device 155, the remote user mobile computing device 170, the remote user computing device 175, or the like) and executing thereon. In some examples, the one or more applications (or portions thereof) may execute in a background of the computing device.

Although various devices in the computing environment 100 are shown and described as separate devices, one or more of the multi-source data evaluation and control computing platform 110, the internal data computing device 120, the external data computing device 140, the first local user computing device 150, the second local user computing device 155, the remote user mobile computing device 170, and/or the remote user computing device 175, may be part of a single computing device without departing from the disclosure.

The internal data computing device 120 may have, store and/or include data obtained by an entity implementing the multi-source data evaluation and control computing platform 110 and/or stored by the entity. In some examples, the internal data computing device 120 may include data associated with customers, one or more insurance claims, accident histories and associated damages, costs, etc., user information, and the like. In some examples, the internal data computing device 120 may include multiple computing devices storing various different types of data. In other examples, the internal data computing device 120 may store the various types of data. In still other examples, the internal data computing device 120 may query databases in one or more other computing devices, systems, or the like, to obtain data that may be used in one or more processes described herein.

The external data computing device 140 may have, store and/or include data from outside of or external to the entity. For instance, the external data computing device 140 may store or provide access to publicly available information, such as weather, traffic, population, demographic information, and the like. Additionally or alternatively, the external data computing device 140 may store or provide access to data related to spending habits of one or more users (e.g., types of purchases made, amounts, locations of purchases, and the like). In still other examples, the external data computing device 140 may store or provide access to data related to behaviors of users, such as frequency of gym visits, data collected by a wearable fitness device, and the like. In other examples, the external data computing device 140 may store or provide access to social data related to users, such as social media posts from social networking services, email messages, text messages, chats, images related thereto, phone calls, contacts, social media friends and/or connections, etc. In some examples, the external data computing device 140 is a computing device of an individual associated with the user (e.g., a friend, connection, relative, individual having a device connected to a device of the user, etc.) and participating in a service provided by the multi-source data evaluation and control system. In some examples, the external data computing device 140 is a computing device of an external service provider which collects (i.e., with appropriate user permissions) and analyzes social data. Various other types of information may be accessed via the external data computing device 140 in some instances. In some examples, the external data computing device 140 may access information from various sources, such as via public network 195.

The first and second local user computing devices 150, 155, the internal data computing system 120, the external data computing system 140, the remote user mobile computing device 170, and the remote user computing device 175 may be configured to communicate with and/or connect to one or more computing devices or systems shown in FIG.

1A. For instance, the first and second local user computing devices 150, 155 and/or the internal data computing device 120 may communicate with one or more computing systems or devices via private network 190, while the remote user mobile computing device 170, the remote user computing device 175, and/or the external data computing device 140 may communicate with one or more computing systems or devices via public network 195. The first and second local user computing devices 150, 155, the remote user mobile computing device 170, and the remote user computing device 175 may be used to configure one or more aspects of the multi-source data evaluation and control computing platform 110, display one or more notifications, execute one or more interactive condition evaluation tests, capture data associated with one or more interactive condition evaluation tests, collect user behavior data and various other types of data, analyze and process the collected data, display outputs, and the like.

In one or more arrangements, the internal data computing device 120, the first local user computing device 150, the second local user computing device 155, the external data computing device 140, the remote user mobile computing device 170, and/or the remote user computing device 175 may be any type of computing device or combination of devices capable of performing the particular functions described herein. For example, the internal data computing device 120, the first local user computing device 150, the second local user computing device 155, the external data computing device 140, the remote user mobile computing device 170, and/or the remote user computing device 175 may, in some instances, be and/or include server computers, desktop computers, laptop computers, tablet computers, smart phones, fitness devices, or the like that may include one or more processors, memories, communication interfaces, storage devices, and/or other components. As noted above, and as illustrated in greater detail below, any and/or all of the multi-source data evaluation and control computing platform 110, the internal data computing device 120, the first local user computing device 150, the second local user computing device 155, the external data computing device 140, the remote user mobile computing device 170, and/or the remote user computing device 175 may, in some instances, be or include special-purpose computing devices configured to perform specific functions.

The computing environment 100 also may include one or more computing platforms. For example, and as noted above, the computing environment 100 may include the multi-source data evaluation and control computing platform 110. As illustrated in greater detail below, the multi-source data evaluation and control computing platform 110 may include one or more computing devices configured to perform one or more of the functions described herein. For example, the multi-source data evaluation and control computing platform 110 may have or include one or more computers (e.g., laptop computers, desktop computers, tablet computers, servers, server blades, or the like).

As mentioned above, the computing environment 100 also may include one or more networks, which may interconnect one or more of the multi-source data evaluation and control computing platform 110, the internal data computing device 120, the first local user computing device 150, the second local user computing device 155, the external data computing device 140, the remote user mobile computing device 170, and/or the remote user computing device 175. For example, the computing environment 100 may include the private network 190 and the public network 195. The private network 190 and/or the public network 195 may include one or more sub-networks (e.g., Local Area Networks (LANs), Wide Area Networks (WANs), or the like).

The private network 190 may be associated with a particular organization (e.g., a corporation, financial institution, educational institution, governmental institution, or the like) and may interconnect one or more computing devices associated with the organization. For example, the multi-source data evaluation and control computing platform 110, the internal data computing device 120, the first local user computing device 150, and/or the second local user computing device 155 may be associated with an organization (e.g., a financial institution), and the private network 190 may be associated with and/or operated by the organization, and may include one or more networks (e.g., LANs, WANs, virtual private networks (VPNs), or the like) that interconnect the multi-source data evaluation and control computing platform 110, the internal data computing device 120, the first local user computing device 150, and/or the second local user computing device 155, and one or more other computing devices and/or computer systems that are used by, operated by, and/or otherwise associated with the organization.

The public network 195 may connect the private network 190 and/or one or more computing devices connected thereto (e.g., the multi-source data evaluation and control computing platform 110, the internal data computing device 120, the first local user computing device 150, or the second local user computing device 155) with one or more networks and/or computing devices that are not associated with the organization. For example, the external data computing device 140, the remote user mobile computing device 170, and/or the remote user computing device 175 may not be associated with an organization that operates the private network 190 (e.g., because the external data computing device 140, the remote user mobile computing device 170, and the remote user computing device 175 may be owned, operated, and/or serviced by one or more entities different from the organization that operates the private network 190, such as one or more customers of the organization, public or government entities, and/or vendors of the organization, rather than being owned and/or operated by the organization itself or an employee or affiliate of the organization). The public network 195 may include one or more networks (e.g., the internet) that connect the external data computing device 140, the remote user mobile computing device 170, and the remote user computing device 175 to the private network 190 and/or one or more computing devices connected thereto (e.g., the multi-source data evaluation and control computing platform 110, the internal data computing device 120, the first local user computing device 150, and/or the second local user computing device 155).

Referring to FIG. 1B, the multi-source data evaluation and control computing platform 110 may include one or more processor(s) 111, one or more memory 112, and one or more communication interface(s) 113. A data bus may interconnect the processor(s) 111, the memory 112, and the communication interface(s) 113.

The communication interface 113 may be a network interface configured to support communication between the multi-source data evaluation and control computing platform 110 and one or more networks (e.g., the private network 190, the public network 195, or the like).

The memory 112 may include one or more program modules having instructions that when executed by the processor(s) 111 cause the multi-source data evaluation and control computing platform 110 to perform one or more functions described herein and/or may include one or more databases that may store and/or otherwise maintain information which may be used by such program modules and/or the processor(s) 111. In some instances, the one or more program modules and/or databases may be stored by and/or maintained in different memory units of the multi-source data evaluation and control computing platform 110 and/or by different computing devices that may form and/or otherwise make up the multi-source data evaluation and control computing platform 110.

The memory 112 may have, store, and/or include a product identification module 112a. The product identification module 112a may store instructions and/or data that may cause or enable the multi-source data evaluation and control computing platform 110 to receive data from, for example, the local user computing device 150, the local user computing device 155, the remote user mobile computing device 170, and/or the remote user computing device 175 that may include a request for a product or service, information about a user requesting the product or service, or for whom the product or service is being requested, and the like. In some examples, the requested product may be a life or other insurance product. In some arrangements, information received may include name and/or other identifiers of a user, age, gender, height, weight, and the like. Additional information, such as the user's email address, social media account information, other account information, and authorization to collect information may also be received. The information may be transmitted from the local user computing devices 150, 155, the remote user mobile computing device 170, the remote user computing device 175, or the like, to the multi-source data evaluation and control computing platform 110 and may be processed by the product identification module 112a to identify one or more products (e.g., a life insurance policy) to offer or recommend to the user. In some examples, interactive tests used to determine eligibility for the one or more products may be identified based on the identified one or more products, as will be discussed more fully herein.

The memory 112 may further have, store, and/or include an interactive test identification module 112b. The interactive test identification module 112b may store instructions and/or data that may cause or enable the multi-source data evaluation and control computing platform 110 to generate or identify one or more interactive condition evaluation tests based on one or more products identified by the product identification module 112a. For instance, one or more interactive condition evaluation tests may be identified for execution by a user. The results of the identified one or more interactive condition evaluation tests may then be used, either alone or in conjunction with other data, for example, user behavior data, to determine whether a user is eligible for the one or more products identified by the product identification module 112a, a cost associated with the one or more products or a component of the one or more products, a deductible associated with the one or more products, a discount or refund that may be available to the user if the user accepts one of the one or more products, and the like. Some example interactive condition evaluation tests may include mobility tests, cognitive skills tests, breathing or other lung capacity tests, and the like. In some examples, the tests may be executed by the user on a mobile device, such as the remote user mobile computing device 170 or the remote user computing device 175. Types of tests, execution of tests, and the like, will be discussed more fully herein.

The memory 112 may further have, store, and/or include an interactive test sensor activation module 112c. The interactive test sensor activation module 112c may store instructions and/or data that may cause or enable the multi-source data evaluation and control computing platform 110 to activate or enable one or more sensors of a plurality of sensors in a computing device, such as the remote user mobile computing device 170, the remote user computing device 175, or the like, for use during one or more of the interactive condition evaluation tests. Some example sensors may include accelerometers, global positioning system (GPS) sensors, gyroscopes, pressure sensors, humidity sensors, pedometers, heart rate sensors, pulse sensors, breathing sensors, one or more cameras or other image capturing devices, and the like. Sensors may also include components of the computing device, such as a usage monitor, or the like, that may record or detect operation of the computing device, applications executed, contact with a display of the computing device, user input, and the like. Upon identifying, by the interactive test identification module 112b, one or more interactive condition evaluation tests to be executed, the interactive test sensor activation module 112c may transmit a signal, instruction, or command to the computing device (e.g., the remote user mobile computing device 170, the remote user computing device 175, or the like) to activate and/or enable one or more sensors. In some examples, the sensors activated or enabled may be sensors identified for use with the identified one or more interactive condition evaluation tests. In some arrangements, the sensors activated or enabled may be fewer than all sensors associated with the computing device.

The memory 112 may further have, store, and/or include an interactive test interface generation module 112d. The interactive test interface generation module 112d may store instructions and/or data that may cause or enable the multi-source data evaluation and control computing platform 110 to generate one or more user interfaces associated with each identified interactive condition evaluation test. For example, for each test identified for execution, by the interactive test identification module 112b, the interactive test interface generation module 112d may generate one or more user interfaces including, for example, information associated with each test, instructions for initiating and/or performing each test, and the like. The interactive test interface generation module 112d may transmit the user interfaces to a computing device, such as the remote user mobile computing device 170, the remote user computing device 175, or the like, and may cause the user interfaces to display on the computing device.

The memory 112 may further have, store, and/or include an interactive test data analysis module 112e. The interactive test data analysis module 112e may store instructions and/or data that may cause or enable the multi-source data evaluation and control computing platform 110 to receive sensor data, from a computing device (e.g., the remote user mobile computing device 170, the remote user computing device 175, or the like) executing one or more interactive condition evaluation tests and analyze the sensor data. In some examples, the interactive test data analysis module 112e may receive raw sensor data collected during one or more of the interactive condition evaluation tests and may process the sensor data (e.g., filter, smooth, or the like) to identify sensor data for analysis (e.g., data to provide the most accurate analysis available). In some examples, one or more machine learning datasets may be used to evaluate or analyze the sensor data processed by the interactive test data analysis module 112e to evaluate a condition of the user executing the tests, as will be discussed more fully herein. In some examples, the sensor data may include data indicating an outcome of a mobility test (e.g., walk a predetermined distance, walk a predetermined time on a treadmill at a designated speed, or the like), an outcome of a reflex analysis test (e.g., how quickly a user responds to a prompt on the computing device), an outcome of one or more cognitive skills tests (e.g., questions directed to evaluating memory, recognition, and the like), an outcome of one or more biometric tests, such as a lung capacity test (e.g., as determined from a force on which a user exhales onto the computing device from a predetermined distance), an outcome of one or more body measurement tests, such as a body mass index (BMI) measurement test, a body composition test, a visceral fat measurement test, a maximum oxygen consumption ($VO_2$ max) test, a metabolic rate test, a waist-to-hip ratio test, etc., an outcome of a blood pressure or heart rate measurement, an outcome of a test detecting a user's smoking status, and the like.

The memory 112 may further have, store, and/or include a user behavior data collection module 112f. The user behavior data collection module 112f may store instructions and/or data that may cause or enable the multi-source data evaluation and control computing platform 110 to receive user behavior data from a plurality of sources, such as the external data computing device 140, the remote user mobile computing device 170, the remote user computing device 175, or other computing devices. In some examples, the user behavior data may be collected from a social networking service, an email server, or the like (e.g., with appropriate user permission). For instance, the user behavior data collection module 112f may scan one or more of the external data computing device 140, the remote user mobile computing device 170, and the remote user computing device 175 to collect behavior data associated with the user. In some examples, the user behavior data collection module 112f may scan social media accounts and/or email accounts associated with the user to collect behavior data of the user. In some examples, the user behavior data collection module 112f may scan other devices associated with the user, such as wearable devices, fitness trackers, etc. The user behavior data collected by the user behavior data collection module 112f may include social media posts from social networking services, email messages, text messages, chats, images, videos, phone calls, contacts, data identifying social media friends and/or connections, data identifying association with affinity groups, organizations, groups, etc. For instance, user behavior data collection module 112f may scan various social networking service accounts associated with the user to collect data, such as comments, images, video, chats, messages, friends/connections, groups associated with, etc. posted by the user. The user behavior data collection module 112f may additionally scan various social networking service accounts of friends, connections, relatives, individuals having devices connected to a device of the user, etc. to collect comments, images, video, chats, messages, friends/connections, etc. related to the user. Further, the user behavior data collection module 112f may scan one or more user computing devices associated with the user, such as the remote user mobile computing device 170 or the remote user computing device 175, or one or more computing devices associated with friends, connections, relatives, individuals having devices connected to a device of the user, etc. to collect data such as emails, text messages, images, videos, phone calls, contacts, chats, membership information, subscription information, etc. stored on the device. The user behavior data may be collected with permission of the user and others associated with the user from whom data is collected, such as friends, connections, relatives, individuals having devices connected to a device of the user, etc. In this case, such friends, connections, relatives, etc. may also participate in the services provided by the multi-source data evaluation and control system. The user behavior data collection module 112f may collect user behavior data from one or more other devices, such as a wearable device or a fitness device, or from one or more application executing on the device, such as a third party application (e.g. a fitness application or the like). For example, the user behavior data collection module 112f may collect step count data or other activity data from a mobile device, wearable device, fitness device, etc. The user behavior data collection module 112f may collect data from one or more additional devices or sources, such as data from electronic health records, from third party or public databases, or the like.

The memory 112 may further have, store, and/or include a user behavior data analysis module 112g. The user behavior data analysis module 112g may store instructions and/or data that may cause or enable the multi-source data evaluation and control computing platform 110 to analyze the user behavior data collected by the user behavior data collection module 112f. The user behavior data collected by the user behavior data collection module 112f may be processed and analyzed to evaluate a user's behavior, habits, lifestyle choices, and health/wellness status. For instance, the collected user behavior data may be scanned for language and images tending to reflect risky and/or positive behavior, habits, or lifestyle choices of the user. For example, images showing or posts commenting on a user smoking or skydiving may tend to reflect risky behavior on the part of the user, while images showing or posts commenting on the user exercising or engaging in healthy eating may tend to reflect positive behavior on the part of the user. Further, research shows that social connections and social interactions play a significant role in an individual's physical and mental well-being and longevity. Such research shows that individuals with meaningful and emotionally healthy relationships are generally happier, have few health-related issues, and live longer lives. Accordingly, the social data collected by the user behavior data collection module 112f may be processed and analyzed to evaluate a user's degree of social connectedness. For instance, the collected user behavior data may be scanned to determine a number of social interactions, such as a number of text messages or emails sent or received, a number of phone calls placed or received, a number of posts made, a number of posts in which the user is referenced, a number of photos posted, a number of photos containing images of the user, a number of friends/connections, a number of individuals followed, a number of followers, etc. However, research further shows that it is the quality of the social connections which counts more than the number of social connections, such that even those with meaningful social connections and unhealthy lifestyles tend to live longer lives than those who have healthier lifestyles but poor social connections. Accordingly, collected user behavior data may be further scanned to evaluate a quality of the user's social connections. For instance, posts containing comments referring to the user's love or affection for a connection or posts referring to the love or affection that a connection may have for the user may tend to show that the social connection is a meaningful one. In some examples, one or more machine learning datasets may be used to analyze the data received from the user behavior data collection module 112f to evaluate a user's behavior, habits, lifestyle choices, health/wellness status.

The user behavior data analysis module 112g may further store instructions and/or data that may cause or enable the multi-source data evaluation and control computing platform 110 to generate a user behavior profile for the user. The user behavior profile may comprise a user behavior score which may be calculated by weighting differently defined categories of analyzed user behavior data. For example, different weighting factors may be used to weigh different categories of analyzed social data. For instance, the different categories of analyzed user behavior data may include: images taken or posted by the user of the user engaging in risky behavior, posts posted by the user describing the user engaging in risky behavior, emails/text messages/chats sent by the user describing the user engaging in risky behavior, images taken by another individual of the user engaging in risky behavior, posts posted by another individual describing the user engaging in risky behavior, emails/text messages/chats sent by another individual to the user describing the user engaging in risky behavior, images taken or posted by the user of the user engaging in positive behavior, posts posted by the user describing the user engaging in positive behavior, emails/text messages/chats sent by the user describing the user engaging in positive behavior, images taken by another individual of the user engaging in positive behavior, posts posted by another individual describing the user engaging in positive behavior, emails/text messages/chats sent by another individual to the user describing the user engaging in positive behavior, text messages sent by the user, text messages received by the user, emails sent by the user, emails received by the user, phone calls placed by the user, phone calls received by the user, chats initiated by the user, chats received by the user, posts posted by the user, posts in which the user is referenced, photos containing images of the user, emails/texts/chats/posts showing meaningful connections, images showing meaningful connections, etc. Each of the different categories may have a different weighting factor associated with the category. For example, categories of user behavior data related to safe behavior may have higher weighting factors than those categories related to risky behavior or those categories indifferent to behavior. The weighting factors may be multiplied by the number of instances of the analyzed user behavior data for each of the different categories of analyzed data to obtain a series of component user behavior scores.

For example, in the case that a first weighting factor is associated with the category of images taken or posted by the user of the user engaging in risky behavior, the first weighting factor may be multiplied by the number of images taken or posted by the user of the user engaging in risky behavior to obtain a first component user behavior score. As another example, in the case that a second weighting factor is associated with the category of emails received by the user, the second weighting factor may be multiplied by the number of emails received by the user to obtain a second component user behavior score. A component user behavior score may be calculated for each category of analyzed social data. The component user behavior scores may be aggregated to determine an overall user behavior score. The overall user behavior score may be a numeric or non-numeric value, such as a number ranging from 1 to 100 or a letter ranging from A to F. The overall user behavior score may be represented in a variety of different ways, e.g., by other numbers or letters, by words, by phrases, etc.

In some examples, the overall user behavior scores may be categorized into groups and ranked. As an example, an overall user behavior score between 1 to 20 may be considered a low score, an overall user behavior score between 21 and 40 may be considered a below average score, an overall user behavior score between 41 and 60 may be considered an average score, an overall user behavior score between 61 and 80 may be considered an excellent score, and an overall user behavior score above 80 may be considered an exceptional score. A low overall user behavior score may reflect a higher level of risk then a higher user behavior score. The user behavior profile may be comprised of the component scores and/or the overall user behavior score and may reflect a determination of a user's risk based on the collected user behavior data. The user behavior profile may be used by the multi-source data evaluation and control computing platform 110 as a factor in a determination of insurance eligibility, an incentive, a discount, and/or at least a component of pricing for a behavior-based variable product or service.

The memory 112 may further have, store, and/or include a supplemental data collection module 112*h*. The supplemental data collections module 112*h* may store instructions and/or data that may cause or enable the multi-source data evaluation and control computing platform 110 to receive various types of data from a plurality of additional sources. For instance, data may be received from one or more internal sources (e.g., internal data computing device 120) and/or from one or more external sources (e.g., external data computing device 140). The data may include data associated with users (e.g., names, addresses, ages, genders, email addresses, social media account information, other account information, and the like), demographic information, locality information, behavioral information (e.g., exercise habits, each habits, etc.), purchase habits or history, medical information, additional behavioral data collected by other sources, and the like. Some or all of the data may be collected with permission of the user. In some examples, one or more machine learning datasets may be used to evaluate the data received from the supplemental data collection module 112*h*, either alone or in conjunction with other data (e.g., sensor data, data from one or more interactive condition evaluation tests, user behavior data, user behavior scores, user behavior profiles, or the like) to determine one or more outputs, as will be discussed more fully herein.

The memory 112 may further have, store, and/or include a data aggregation module 112*i*. The data aggregation module 112*h* may store instructions and/or data that may cause or enable the multi-source data evaluation and control computing platform 110 to aggregate the data collected and analyzed from the various sources, e.g., sensor data, test data, user behavior data, supplemental data, etc. In some examples, one or more machine learning datasets may be used to evaluate the aggregated data to determine one or more outputs.

The memory 112 may further have, store, and/or include a machine learning engine 112*j* and machine learning datasets 112*k*. Machine learning engine 112*j* and machine learning datasets 112*k* may store instructions and/or data that cause or enable the multi-source data evaluation and control computing platform 110 to evaluate data, such as sensor data, test data, user behavior data, user behavior scores, user behavior profiles, supplemental data, aggregated data, and the like, to generate or determine one or more outputs (e.g., by output generation module 112*l*). The machine learning datasets 112*k* may be generated based on analyzed data (e.g., data from previously executed interactive condition evaluation tests, previously analyzed user behavior data, scores, and profiles, historical data from internal and/or external sources, and the like), raw data, and/or data received from one or more outside sources.

The machine learning engine 112*j* may receive data (e.g., user behavior data, scores, profiles, data collected during one or more interactive condition evaluation tests executed by and received from, for example, the remote user mobile computing device 170, the remote user computing device 175, the internal data computing device 120, the external data computing device 140, and the like, supplemental data received from various other sources, and/or aggregated data) and, using one or more machine learning algorithms, may generate one or more machine learning datasets 112k. Various machine learning algorithms may be used without departing from the disclosure, such as supervised learning algorithms, unsupervised learning algorithms, regression algorithms (e.g., linear regression, logistic regression, and the like), instance based algorithms (e.g., learning vector quantization, locally weighted learning, and the like), regularization algorithms (e.g., ridge regression, least-angle regression, and the like), decision tree algorithms, Bayesian algorithms, clustering algorithms, artificial neural network algorithms, and the like. Additional or alternative machine learning algorithms may be used without departing from the disclosure. In some examples, the machine learning engine 112j may analyze data to identify patterns of activity, sequences of activity, and the like, to generate one or more machine learning datasets 112k.

The machine learning datasets 112k may include machine learning data linking one or more outcomes of an interactive condition evaluation test, types or amounts of sensor data, historical user behavioral data, scores, and/or profiles, transaction data, health data, supplemental data, or the like (or combinations thereof) to one or more outputs. For instance, data may be used to generate one or more machine learning datasets 112k linking data from interactive condition evaluation tests, internal user data, external user data, user behavior data, scores, and/or profiles, supplemental data, and the like, to outputs, such as a mortality rate, likelihood of developing one or more illnesses or diseases, likelihood of risk-taking behavior, health/wellness status, and the like. This information may be used to evaluate a risk associated with a user requesting a product or service (e.g., a life insurance product or service) to determine a premium or deductible of an insurance policy, a discount, rebate or other incentive to offer to the user, and the like. The information may additionally be used to evaluate a risk and/or a health/wellness status associated with a user to determine at least a component of pricing for the behavior-based variable product or service (e.g., an auto, life, or home insurance product or service).

The machine learning datasets 112k may be updated and/or validated based on later-received data. For instance, as additional interactive condition evaluation tests are executed, as additional user behavior data is collected and user behavior scores are calculated and user behavior profiles are generated, as supplemental data is collected or received from internal data computing device 120, external data computing device 140, and the like, the machine learning datasets 112k may be validated and/or updated based on the newly received information. Accordingly, the system may continuously refine determinations, outputs, and the like.

The machine learning datasets 112k may be used by, for example, an output generation module 112l stored or included in memory 112. The output generation module 112l may store instructions and/or data configured to cause or enable the multi-source data evaluation and control computing platform 110 to generate one or more outputs based on the machine learning dataset 112k analysis of data (e.g., sensor data, user behavior data, scores, and profile, supplemental data, aggregated data, and the like). For instance, as discussed above, the output generation module 112l may generate one or more premiums, discounts, incentives, pricing, or the like, related to a product or service identified for a user, requested by a user, an existing product or service of the user, or the like. In some examples, the output generation module 112l may transmit the generated output to a computing device, such as the remote user mobile computing device 170, the remote user computing device 175, or the like, and may cause the generated output to display on the device. In some arrangements, the output may be transmitted to the computing device from which the user requested a product, on which the one or more interactive condition evaluation tests were executed, the user behavior data was collected, or the like.

Figure 2:
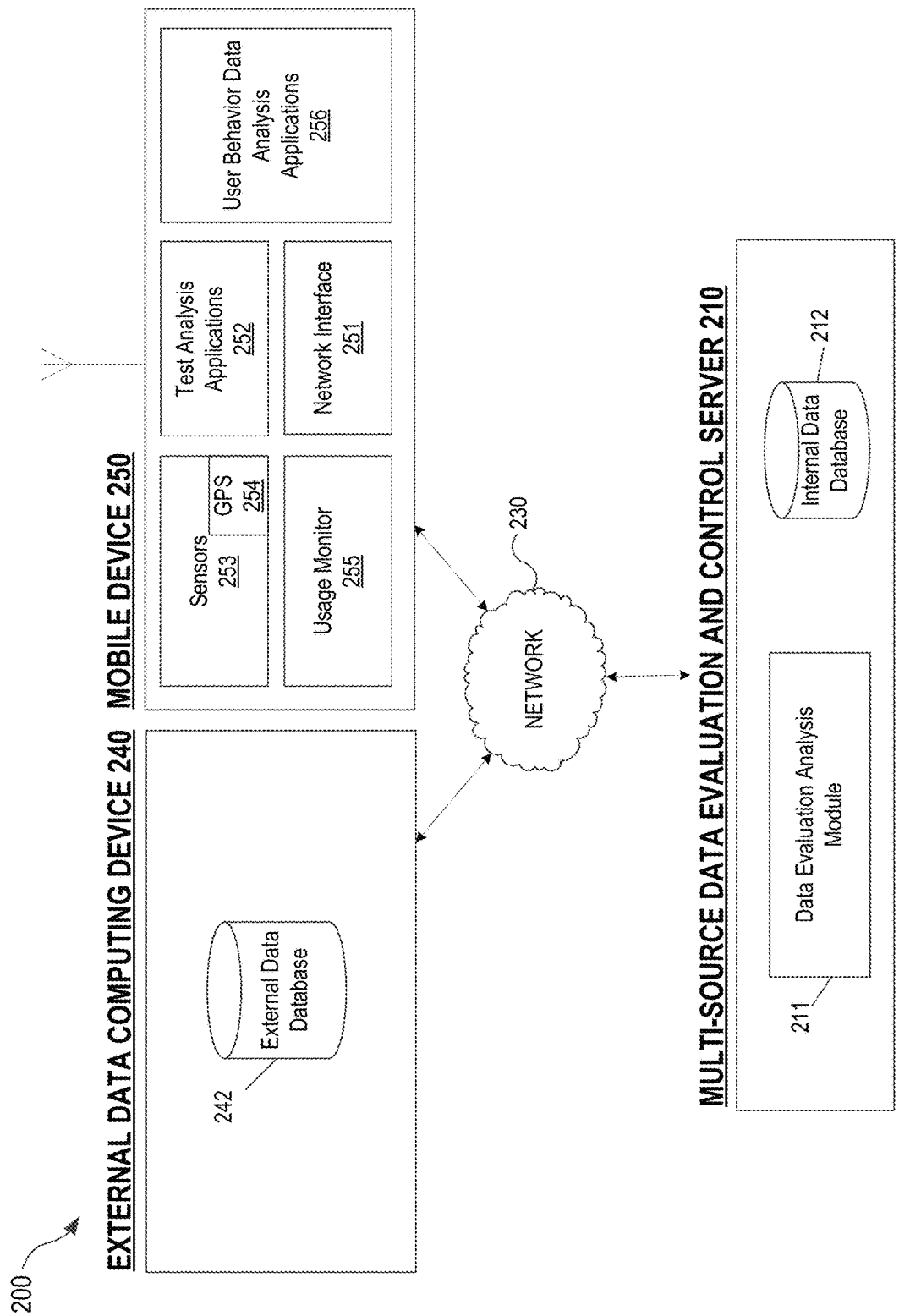
FIG. 2 illustrates an example multi-source data evaluation and control computing system, according to one or more aspects described herein.

FIG. 2 is a diagram of an illustrative multi-source data evaluation and control system 200 including a multi-source data evaluation and control server 210, an external computing device 240, a mobile device 250, and additional related components. Each component shown in FIG. 2 may be implemented in hardware, software, or a combination of the two. Additionally, each component of the multi-source data evaluation and control system 200 may include a computing device (or system) having some or all of the structural components described herein for computing device 901 shown in FIG. 9. The multi-source data evaluation and control system 200 may also include or be in communication with one or more computing platforms, servers, devices, and the like, shown and described with respect to FIGS. 1A and 1B.

One or more components shown in FIG. 2, the multi-source data evaluation and control server 210, the external data computing device 240, and/or the mobile device 250 may communicate with each other via wireless networks or wired connections, and each may communicate with additional mobile computing devices, other remote user computing devices (e.g., the remote user computing device 170) and/or a number of external computer servers, devices, etc. over one or more communication networks 230. In some examples, the mobile computing device 250 may be paired (e.g., via Bluetooth™ technology) to one or more other devices (e.g., another user personal mobile computing device, such as a wearable device, tablet, etc.). If the device is no longer in proximity to be paired (e.g., the mobile computing device 250 is no longer near enough to another user personal mobile computing device to be paired) a notification may be generated and displayed on the mobile computing device 250 (e.g., to indicate that a device may have been left behind).

As discussed herein, the components of the multi-source data evaluation and control system 200, operating individually or using communication and collaborative interaction, may perform such features and functions such as identifying one or more products or services, identifying one or more interactive condition evaluation tests, executing one or more interactive condition evaluation tests, collecting data associated with one or more interactive condition evaluation tests, collecting user behavior data, calculating user behavior scores, generating a user behavior profile, retrieving supplemental data from one or more internal and/or external sources, aggregating collected and analyzed data, generating an output, and the like.

The multi-source data evaluation and control system 200 may include one or more mobile devices 250, for example, smartphones or other mobile phones, personal digital assistants (PDAs), tablet computers, laptop computers, wearable devices, such as smart watches and fitness monitors, and the like. Mobile device 250 may include some or all of the elements described herein with respect to the computing device 901.

The mobile device 250 may include a network interface 251, which may include various network interface hardware (e.g., adapters, modems, wireless transceivers, etc.) and software components to enable the mobile device 250 to communicate with the multi-source data evaluation and control server 210, the external computing device 240, and various other external computing devices. One or more specialized software applications, such as test analysis applications 252 and user behavior data analysis applications 256 may be stored in the memory of the mobile device 250.

The test analysis applications 252 may be received, via the network interface 251, from the multi-source data evaluation and control server 210, or other application providers (e.g., public or private application stores). Certain test analysis applications 252 might not include user interface screens, while other test analysis applications 252 may include user interface screens that support user interaction. Such test analysis applications 252 may be configured to run as user-initiated applications or as background applications.

The user behavior data analysis applications 256 may be received, via the network interface 251, from the multi-source data evaluation and control server 210, or other application providers (e.g., public or private application stores). Certain user behavior data analysis applications 256 might not include user interface screens, while other user behavior data analysis applications 256 may include user interface screens that support user interaction. Such user behavior data analysis applications 256 may be configured to run as user-initiated applications or as background applications.

The memory of the mobile device 250 also may include databases configured to store sensor data received from mobile device sensors, usage type data, application usage data, user behavior data, scores, and profiles, supplemental data, and the like received from one or more additional devices/sources, social networking services, email servers, and the like.

Although aspects of the test analysis applications 252 and the user behavior analysis applications 256 are described as executing on the mobile device 250, in various other implementations, some or all of the test analysis functionality described herein may be implemented by the multi-source data evaluation and control server 210. As discussed herein, the mobile device 250 may include various components configured to generate and/or receive data associated with execution of one or more interactive condition evaluation tests by or on the mobile device 250, and/or data associated with usage of the mobile device 250. For example, using data from sensors 253 (e.g., 1-axis, 2-axis, or 3-axis accelerometers, compasses, speedometers, vibration sensors, pressure sensors, gyroscopic sensors, etc.) and/or GPS receivers or other location-based services (LBS) 254, the test analysis application 252 (or other device or module, e.g., multi-source data evaluation and control server 210) may determine movement of the mobile device 250, evaluate actions performed with or on the mobile device 250, and the like. The sensors 253 and/or GPS receivers or the other LBS services 254 of the mobile device 250 may also be used to determine speeds (e.g., walking pace, running pace, etc.), force on the mobile device 250, response times for providing input to the mobile device 250, and the like.

The mobile device 250 may further include a usage monitor 255. The usage monitor 255 may be a computing device (e.g., including a processor, computing, etc.) and may include hardware and/or software configured to monitor various aspects of the usage of the mobile device 250. For instance, the usage monitor 255 may monitor a number of minutes, hours, or the like the mobile device 250 is in use (e.g., based on factors such as the device being illuminated, a user interacting with or looking at the device, etc.). Further, the usage monitor 255 may monitor which applications are used above a threshold amount of time in a predetermined time period (e.g., one day, one week, one month, or the like). In still other examples, the usage monitor 255 may determine a type of motion or a speed of motion associated with movement of the mobile device 250, whether the mobile device 250 is maintained within a case, and the like. Additional aspects of device usage may be monitored without departing from the disclosure. Data related to usage of the mobile device 250 may be used to determine one or more outputs (e.g., may indicate decreased mobility, inactive lifestyle, and the like).

The mobile device 250 may be configured to establish communication with the multi-source data evaluation and control server 210 via one or more wireless networks (e.g., the one or more communication networks 230).

The multi-source data evaluation and control system 200 may further include an external data computing device 240. The external data computing device 240 may store or receive data from one or more external data sources, such as user information, health information, automotive information (e.g., driving behaviors, operational parameters, make, model, trim, etc.), transaction information, user behavioral information, supplemental information, and the like. This information may be aggregated and processed, for instance, by the multi-source data evaluation and control server 210, to generate one or more outputs. The external data computing device 240 may include an external data database 242 that may store data from one or more external sources for use in generating one or more outputs.

Figure 9:
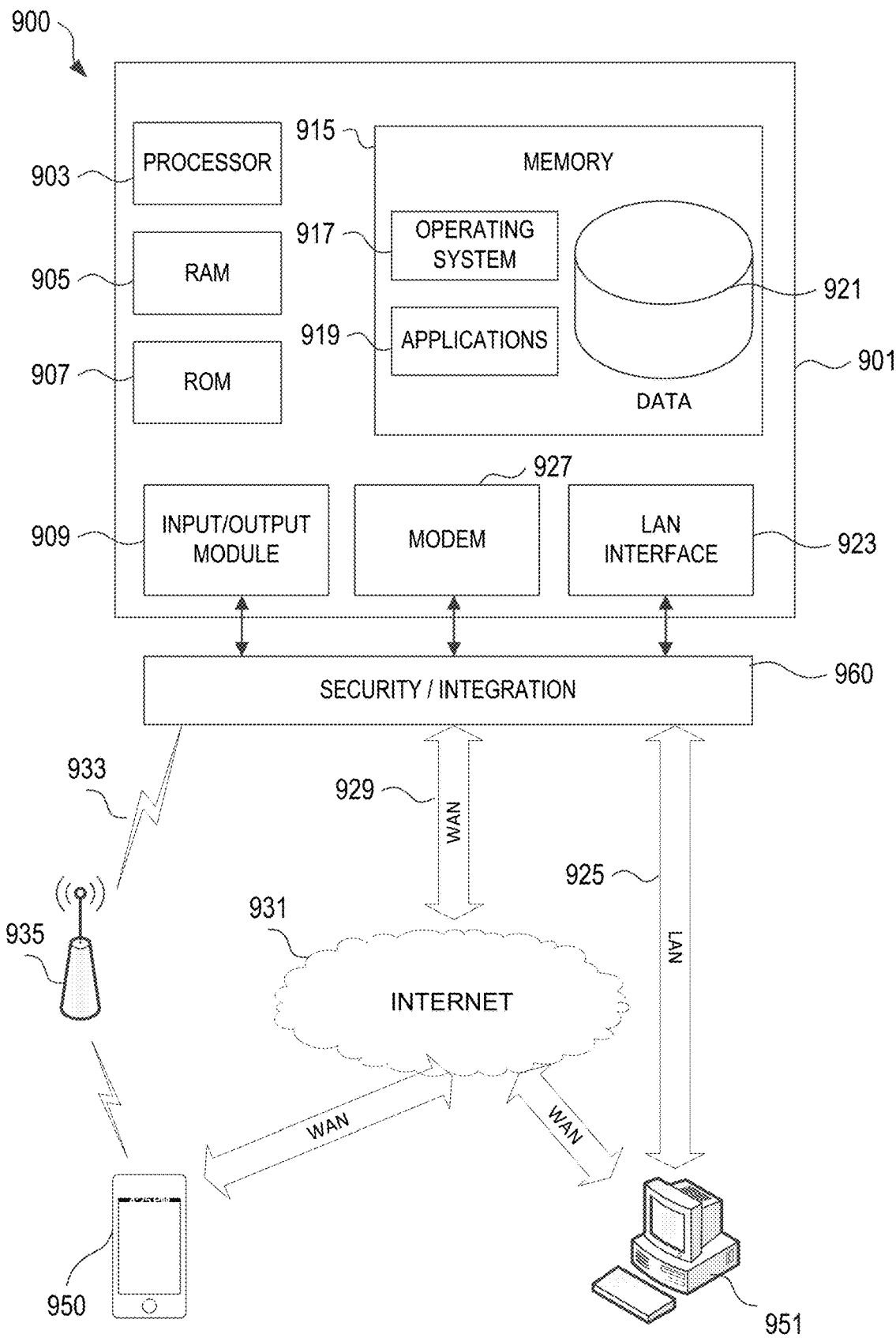
FIG. 9 illustrates a network environment and computing systems that may be used to implement aspects of the disclosure.

The multi-source data evaluation and control system 200 also may include one or more external servers, such as multi-source data evaluation and control server 210 which may contain some or all of the hardware/software components as the computing device 901 depicted in FIG. 9. The multi-source data evaluation and control server 210 may additionally or alternatively include some or all of the components and/or functionality described with respect to FIGS. 1A and 1B. The multi-source data evaluation and control server 210 may include one or more internal data databases 212 configured to store data associated with, for example, data internal to an entity (e.g., user or customer data, historical data relating to claims, accidents, user behavior data, and the like), that may be used to evaluate risk. Further, the multi-source data evaluation and control server 210 may include a data evaluation analysis module 211 which may provide some or all of the operations and/or functionality described with respect to FIGS. 1A and 1B.

FIGS. 3A-3I illustrate one example event sequence for executing one or more interactive condition evaluation tests, collecting and analyzing user behavior data, and determining an output in accordance with one or more aspects described herein. The sequence illustrated in FIGS. 3A-3I is merely one example sequence and various other events may be included, or events shown may be omitted, without departing from the disclosure.

Figure 3A:
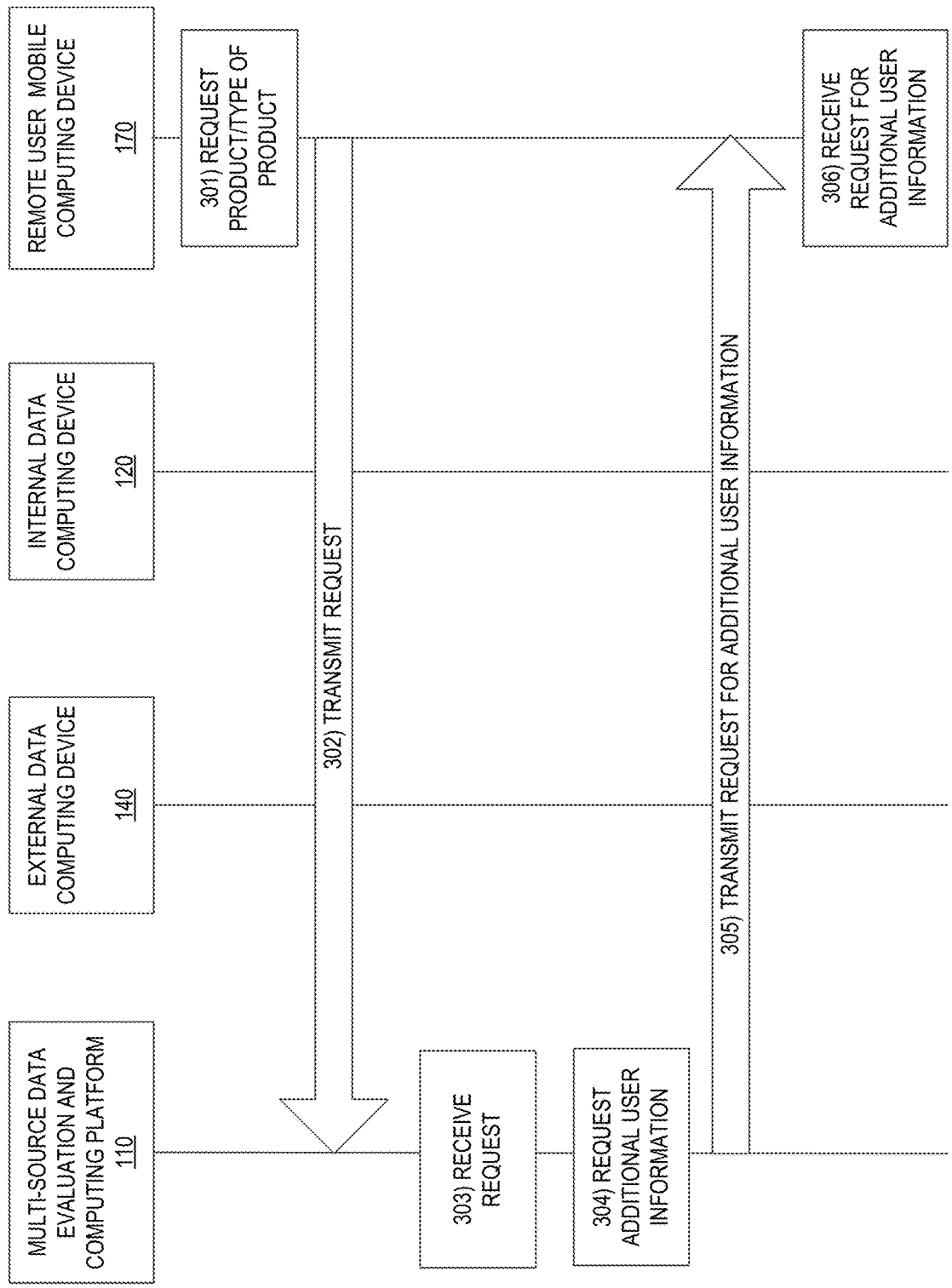

With reference to FIG. 3A, in step 301, a request for a particular product or service, or type of product or service may be received by a user computing device, such as the remote user mobile computing device 170. The request may include a request to purchase the particular product or service. In some examples, the request may include information associated with a user for whom the request is made (e.g., name, contact information, and the like). Alternatively, if the user has an existing product or service, a request to identify the existing product or service may be received.

In step 302, the request may be transmitted from the remote user mobile computing device 170 to the multi-source data evaluation and control computing platform 110.

The request may be received by the multi-source data evaluation and control computing platform 110 in step 303 and the multi-source data evaluation and control computing platform 110 may process the request.

In step 304, a request for additional user information may be generated. The request may include a request for information associated with the particular user, such as age, gender, location, occupation, tobacco usage, email address, social media account information, other account information, and the like. The request may additionally include a request for authorization to collect user behavior data from a user's social media accounts, email accounts, the remote user mobile computing device 170, and other devices associated with the user, such as fitness devices, wearable devices, etc. The request may additionally include a request for authorization to collect user behavior data from the social media accounts and devices of friends/connections of the user who also participate in the service provided by the multi-source data evaluation and control system and who have independently agreed to have user behavior data collected from their social media accounts and devices.

In step 305, the request for additional user information may be transmitted to the remote user mobile computing device 170 and, in step 306, the request for additional information may be received by the remote user mobile computing device 170.

Figure 3B:
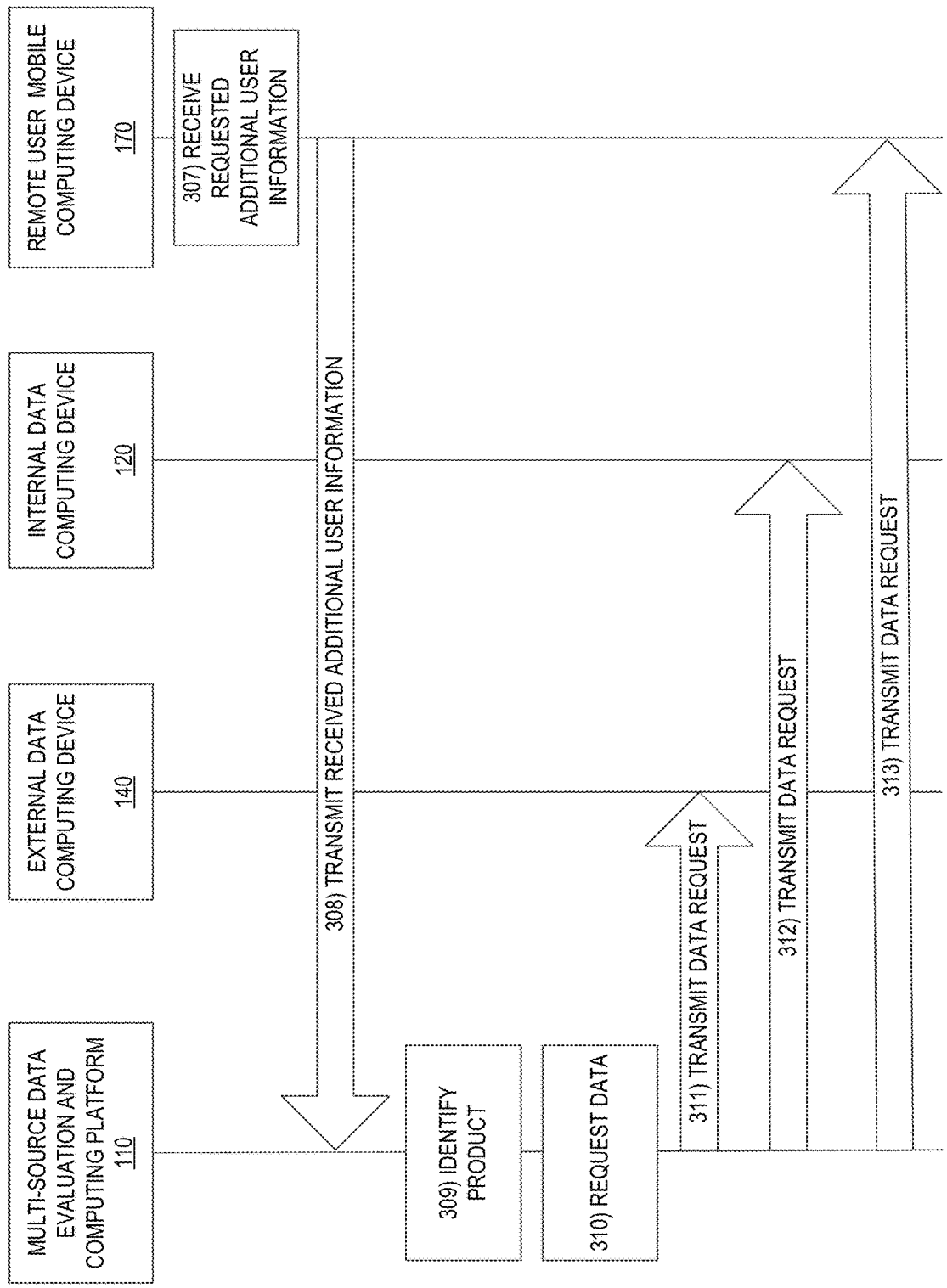

With reference to FIG. 3B, in step 307, the requested additional user information may be received by the remote user mobile computing device 170.

In step 308, the received additional user information may be transmitted to the multi-source data evaluation and control computing platform 110. In some examples, steps 301 through 308 may be optional, such as for an automatic determination of user eligibility.

In step 309, the received additional user information may be processed to identify one or more products or services to offer to the user that meet the request provided by the user (e.g., if the user has requested a life insurance policy, the multi-source data evaluation and control computing platform 110 may identify one or more life insurance policies that may be suitable for the user based on the user information and that may be offered to the user) or to identify one or more existing products or services (e.g., a behavior-based variable product or service) to reevaluate for user eligibility for pricing adjustments, incentives, discounts, rebates, etc. In the case where the user has one or more existing products or services, step 309 may be initiated automatically on a periodic basis (e.g., daily, weekly, monthly, on a predetermined schedule, etc.) to identify those products and services of the user which require revaluation. In this case, step 309 may be performed without the additional user information and without the need to perform steps 301 to 308. When step 309 is initiated automatically on a periodic basis, the multi-source data evaluation and control computing platform 110 may identify the one or more existing products or services requiring reevaluation after determining that a predetermined time, associated with the periodic schedule, has elapsed since the product or service was last evaluated for eligibility or since the product or service was purchased.

In step 310, a request for data may be generated. For instance, the multi-source data evaluation and control computing platform 110 may generate one or more requests for data associated with the user. The requests may include data related to health information of the user, spending habits or other transaction information, lifestyle information, driving behaviors, insurance claim information, user behavior data, and the like. The data requests may be transmitted to the external data computing device 140 in step 311 to the internal data computing device 120 in step 312, and/or to the remote user mobile computing device 170 in step 313. In some examples, requests for data may be transmitted to additional computing devices. In some arrangements, the requests for data may include a name or other unique identifier of a user that may be used as input in a query to identify the desired data.

With reference to FIG. 3C, the request for data may be received by the external data computing device 140 in step 314, the internal data computing device 120 in step 315, and/or the remote user mobile computing device 170 in step 316.

In steps 317, 318, and 319, the requested data may be extracted from the external data computing device 140, the internal data computing device 120, and/or the remote user mobile computing device 170, respectively.

In steps 320, 321, and 322, extracted data may be transmitted to the multi-source data evaluation and control computing platform 110 from the from the external data computing device 140, the internal data computing device 120, and/or the remote user mobile computing device 170, respectively.

Figure 3D:
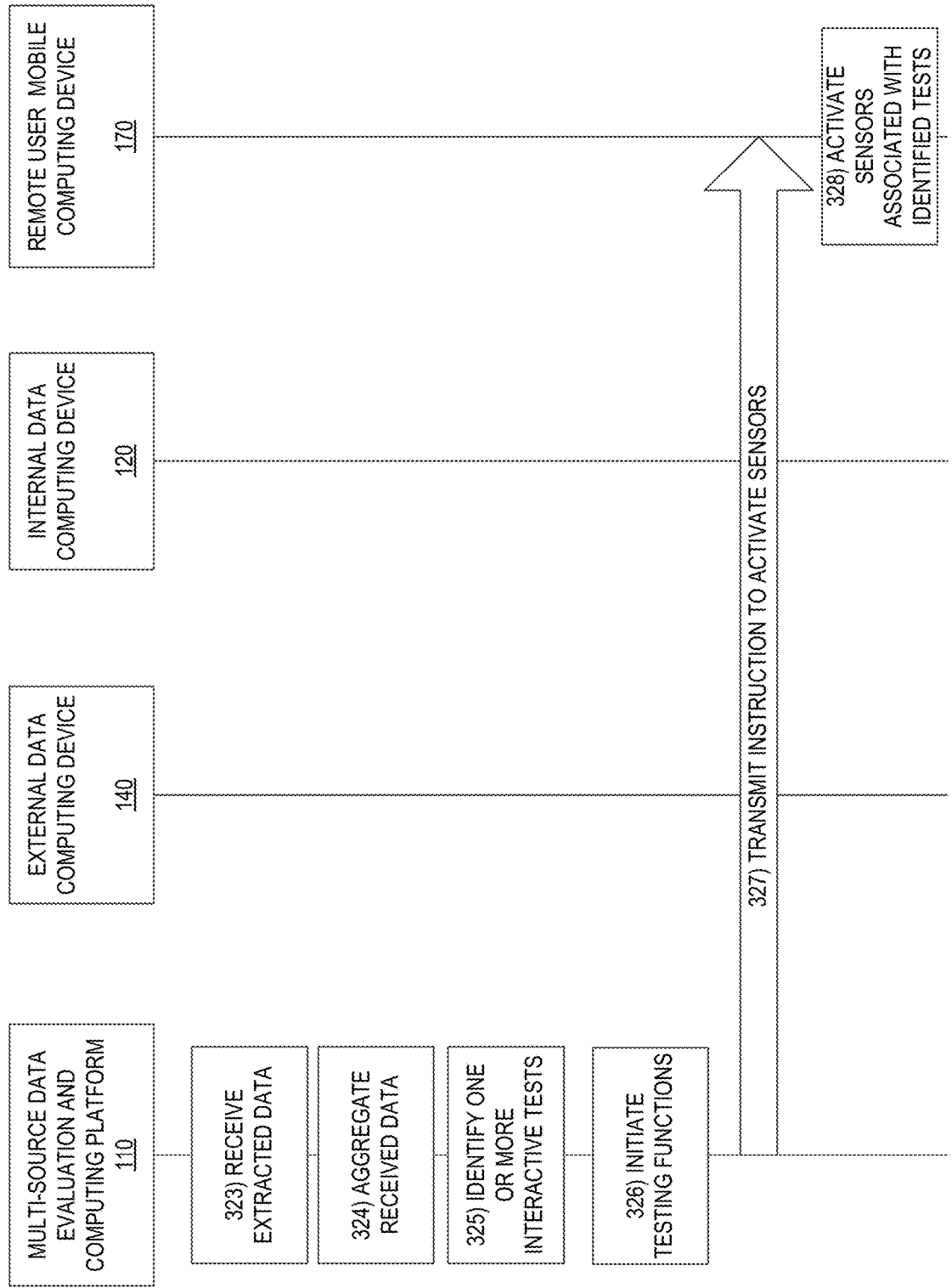

With reference to FIG. 3D, in step 323, the extracted data may be received and, in step 324, the extracted data may be aggregated. In some examples, step 324 of aggregating the data may be optional.

In step 325, one or more interactive condition evaluation tests to determine eligibility for the one or more identified products may be identified. For instance, based on the one or more products or services identified for the user, one or more interactive condition evaluation tests may be identified. In some examples, a plurality of different types of interactive condition evaluation tests may be stored and, in step 325, one or more of the plurality of tests may be selected or identified for execution on the remote user mobile computing device 170. Particular types of tests will be discussed more fully herein.

For instance, data associated with the user may be used to identify one or more products or services to offer to the user or one or more existing products or services of the user, and the identified one or more products or services may be used to identify one or more interactive condition evaluation tests to execute. In some examples, user information (e.g., age, health information, and the like) may also be used in identifying one or more interactive condition evaluation tests to and/or in determining parameters of one or more interactive condition evaluation tests. For instance, if the system identifies a first test as a timed treadmill test in which a user must walk on a treadmill for a predetermined distance (as measured by the remote user mobile computing device 170), the required distance may be modified based on an age of the user and/or an expected time (or time to fit into a particular category) may be modified based on the age of the user. Accordingly, in one example, a 65 year old user may be given a test having a shorter distance or a shorter expected time than a 25 year old user.

In step 326, one or more interactive condition evaluation test functions may be initiated by the multi-source data evaluation and control computing platform 110. For instance, upon identifying one or more interactive condition evaluation tests for execution, one or more functions associated with administering the tests (e.g., generating interfaces including instructions, transmitting interfaces, processing received data, and the like) may be enabled or activated by or within the multi-source data evaluation and control computing platform 110. In some examples, upon completion of the testing process (e.g., upon generating an output) the enabled or activated functions may be disabled or deactivated in order to conserve computing resources.

In step 327, an instruction to activate one or more sensors in the remote user mobile computing device 170 may be generated and transmitted to the remote user mobile computing device 170. For instance, upon identifying one or more interactive condition evaluation tests for execution by the remote user mobile computing device 170, the multi-source data evaluation and control computing platform 110 may identify one or more sensors associated with the remote user mobile computing device 170 that may be used to collect data associated with the identified tests and may transmit an instruction to the remote user mobile computing device 170 to activate or enable the identified sensors.

In step 328, the instruction may be received by the remote user mobile computing device 170 and may be executed to activate the identified sensors.

Figure 3E:
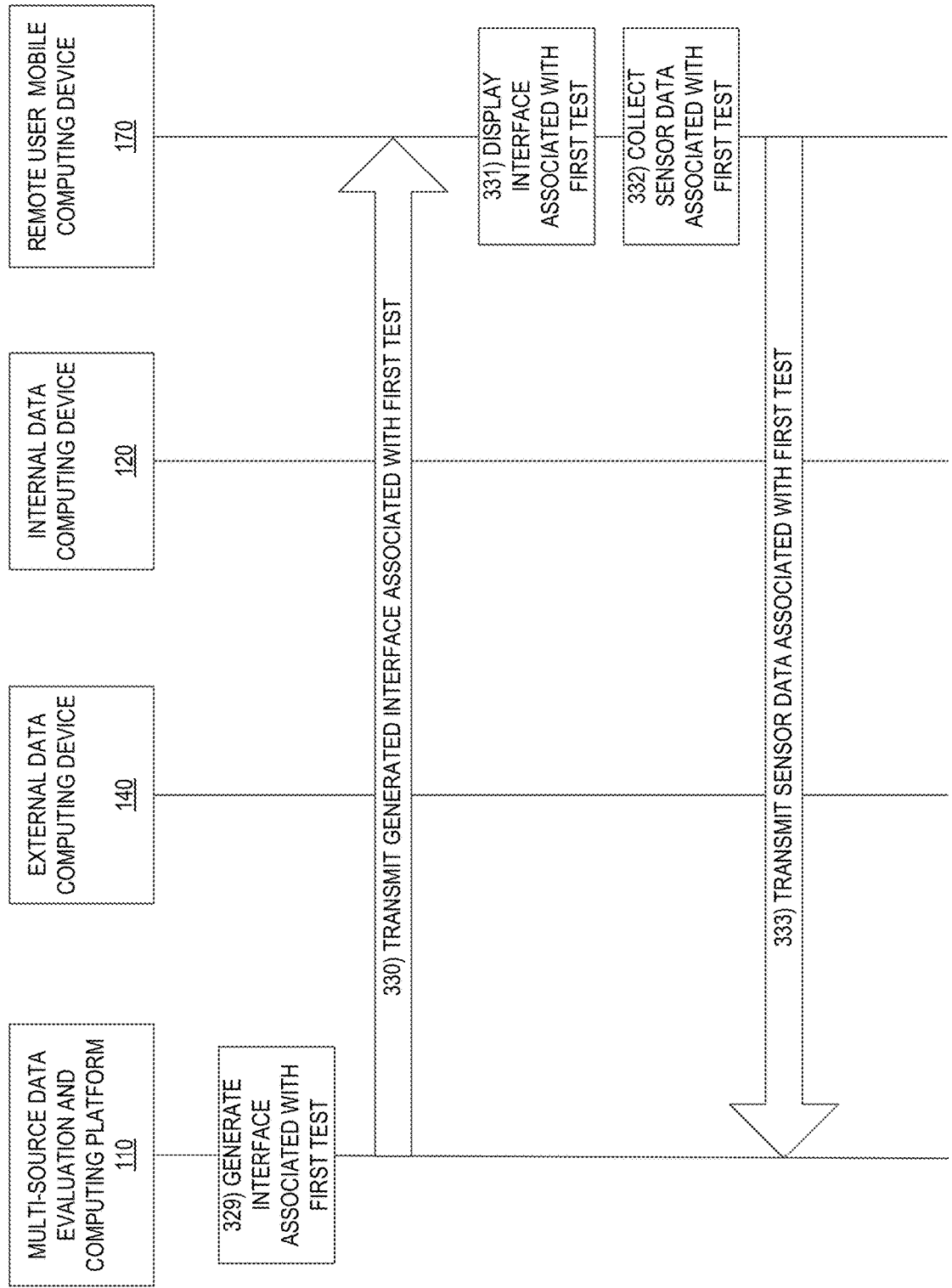

With reference to FIG. 3E, in step 329, a user interface associated with a first test of the identified one or more interactive condition evaluation tests may be generated. In some examples, the user interface may include instructions for executing the first test. In some examples, the user interface may be a link to a mobile application which in turn provides a user interface for executing the first test on the remote user mobile computing device 170.

In step 330, the generated user interface associated with the first test may be transmitted to the remote user mobile computing device 170 and, in step 331, the user interface may be displayed on a display of the remote user mobile computing device 170.

In step 332, the first test may be initiated and sensor data associated with the first test may be collected. For instance, data from one or more sensors monitoring movement, speed, position, and the like, of the remote user mobile computing device 170 or the user may be collected. In some examples, data may be collected based on an interaction with one or more user interfaces (e.g., response times, etc.).

In step 333, the sensor data associated with the first test may be transmitted from the remote user mobile computing device 170 to the multi-source data evaluation and control computing platform 110.

Figure 3F:
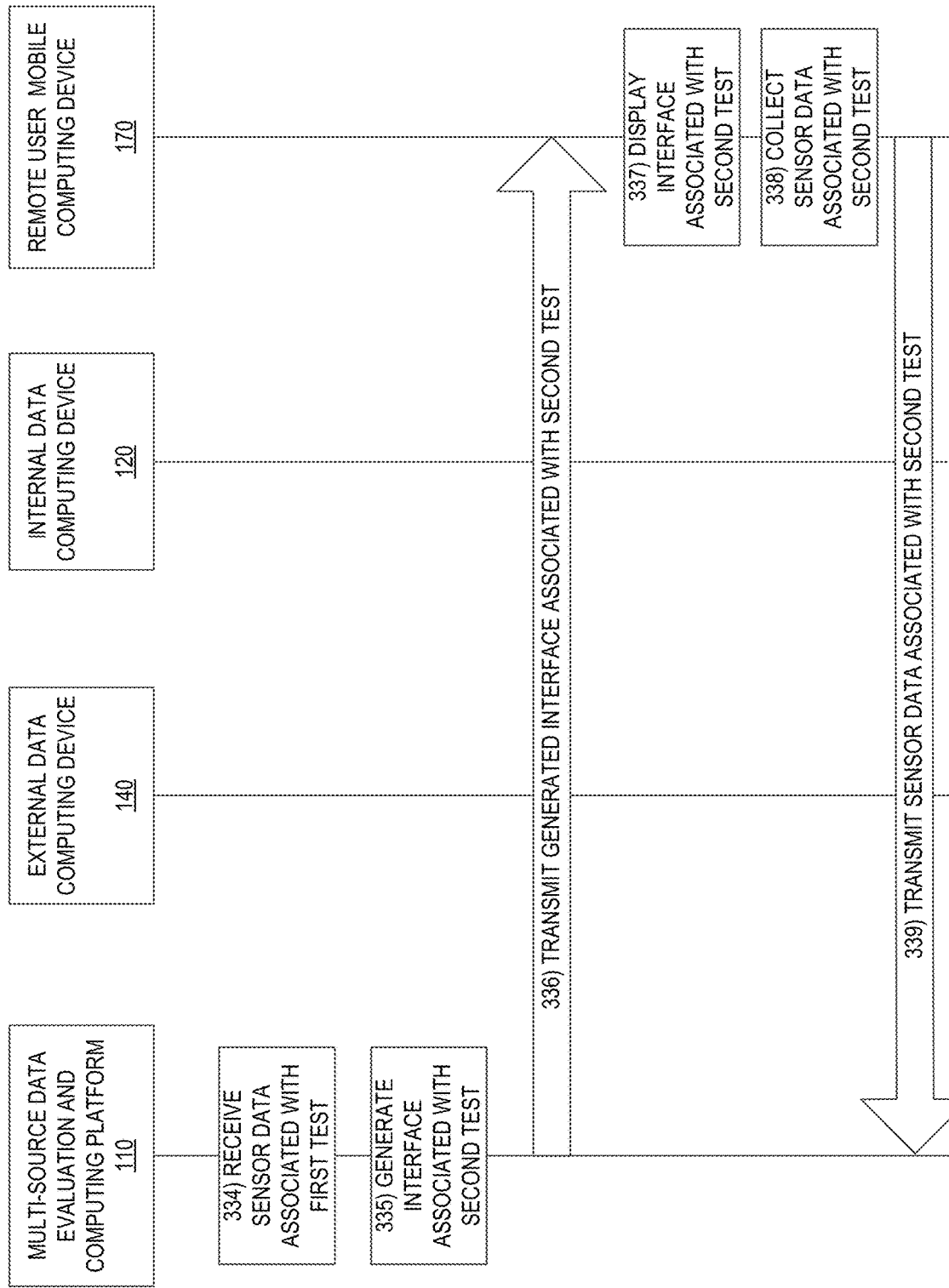

With reference to FIG. 3F, the sensor data associated with the first test may be received in step 334.

In step 335, if additional tests have been identified for execution, a user interface for a second interactive condition evaluation test may be generated. The user interface may include instructions and/or parameters for executing the second interactive condition evaluation test by or with the remote user mobile computing device 170.

In step 336, the user interface associated with the second test may be transmitted to the remote user mobile computing device 170 and, in step 337, the user interface may be displayed on a display of the remote user mobile computing device 170. In some examples, the user interface may be a link to a mobile application which in turn provides a user interface for executing the second test on the remote user mobile computing device 170.

In step 338, sensor data associated with execution of the second interactive condition evaluation test may be collected and, in step 339, the collected sensor data may be transmitted to the multi-source data evaluation and control computing platform 110.

Figure 3G:
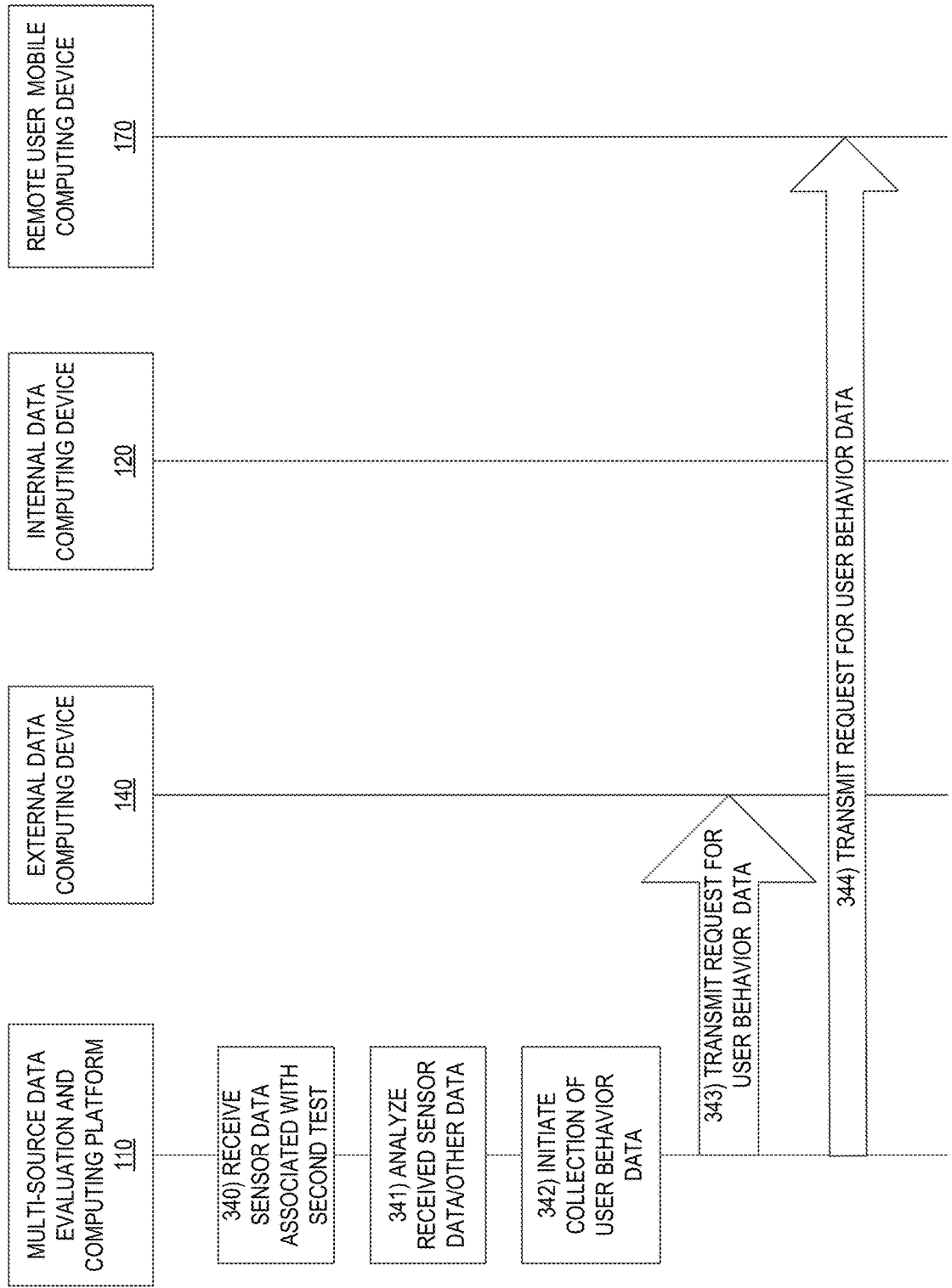

With reference to FIG. 3G, in step 340, sensor data associated with the second interactive condition evaluation test may be received.

In step 341, the received sensor data (e.g., from the first test, second test, and any other tests) and/or other data (e.g., data from the internal data computing device 120, data from the external data computing device 140, data from the remote user mobile computing device 170, and the like) may be analyzed. In some examples, analyzing the data may include comparing the data to one or more machine learning datasets. In some examples, steps 325 to 341 may be optional, such as for an eligibility determination for pricing or adjustment thereof of an existing product or service, e.g., a behavior-based variable product. In such cases, collection and processing of only user behavior data and/or supplemental data may be necessary to make the determination.

In step 342, user behavior data collection may be initiated by the multi-source data evaluation and control computing platform 110. The multi-source data evaluation and control computing platform 110 may identify a type of user behavior data to collect based on the product or service identified in step 309. For instance, the multi-source data evaluation and control computing platform 110 may determine to collect user behavior data such as social media posts and comments from social networking services, email messages, text messages, chats, images, videos, phone calls, contacts, social media friends/connections, etc. based on the identified product or service. Certain types of user behavior data may be collected for certain products and services, and other types of user behavior data may be collected for other products and services. For instance, the multi-source data evaluation and control computing platform 110 may cause one or more of the internal data computing device 120, the external data computing device 140, the remote user mobile computing device 170, or other computing device to be scanned to collect (i.e., with appropriate user permission) user behavior data of the identified type associated with the user. The multi-source data evaluation and control computing platform 110 may scan various social networking service accounts, email accounts, and devices associated with the user to collect the user behavior data. The multi-source data evaluation and control computing platform 110 may additionally scan various social networking service accounts and devices of friends, connections, relatives, individuals having devices connected to a device of the user, etc. to collect user behavior data related to the user. The user behavior data may be collected with permission of the user and others associated with the user from whom data is collected, such as friends, connections, relatives, individuals having devices connected to a device of the user, etc.

The multi-source data evaluation and control computing platform 110 may transmit a request for user behavior data to the external data computing device 140 in step 343 and/or the remote user mobile computing device 170 in step 344. In some examples, the external data computing device 140 is a computing device of an individual associated with the user (e.g., a friend, connection, relative, individual having a device connected to a device of the user, etc.) and participating in a service provided by the multi-source data evaluation and control system. In some examples, requests for the user behavior data may be transmitted to additional computing devices, such as the internal data computing device 120 or other devices. In some arrangements, the requests for the user behavior data may include a name or other unique identifier of a user, such as an email address, social media or other account information, etc. that may be used as input in a query to identify the user behavior data.

Figure 3H:
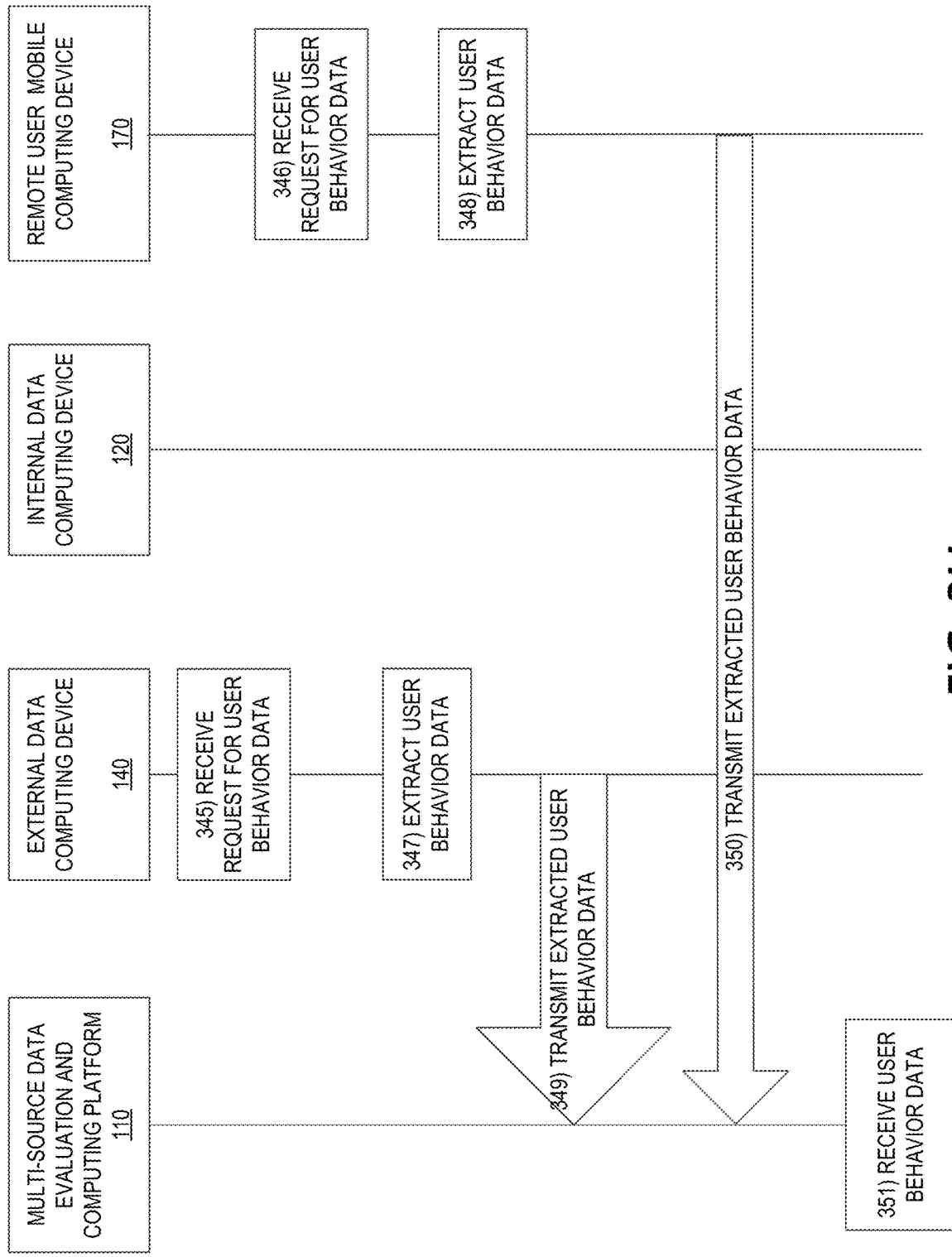

Referring to FIG. 3H, the request for the user behavior data may be received by the external data computing device 140 in step 345 and by the remote user mobile computing device 170 in step 346.

In steps 347 and 348, the user behavior data may be extracted from the external data computing device 140 and the remote user mobile computing device 170, respectively.

In steps 349 and 350, the user behavior data extracted from the external data computing device 140 and the remote user mobile computing device 170, respectively, may be transmitted to the multi-source data evaluation and control computing platform 110. In step 351, the extracted user behavior data may be received by the multi-source data evaluation and control computing platform 110.

Figure 3I:
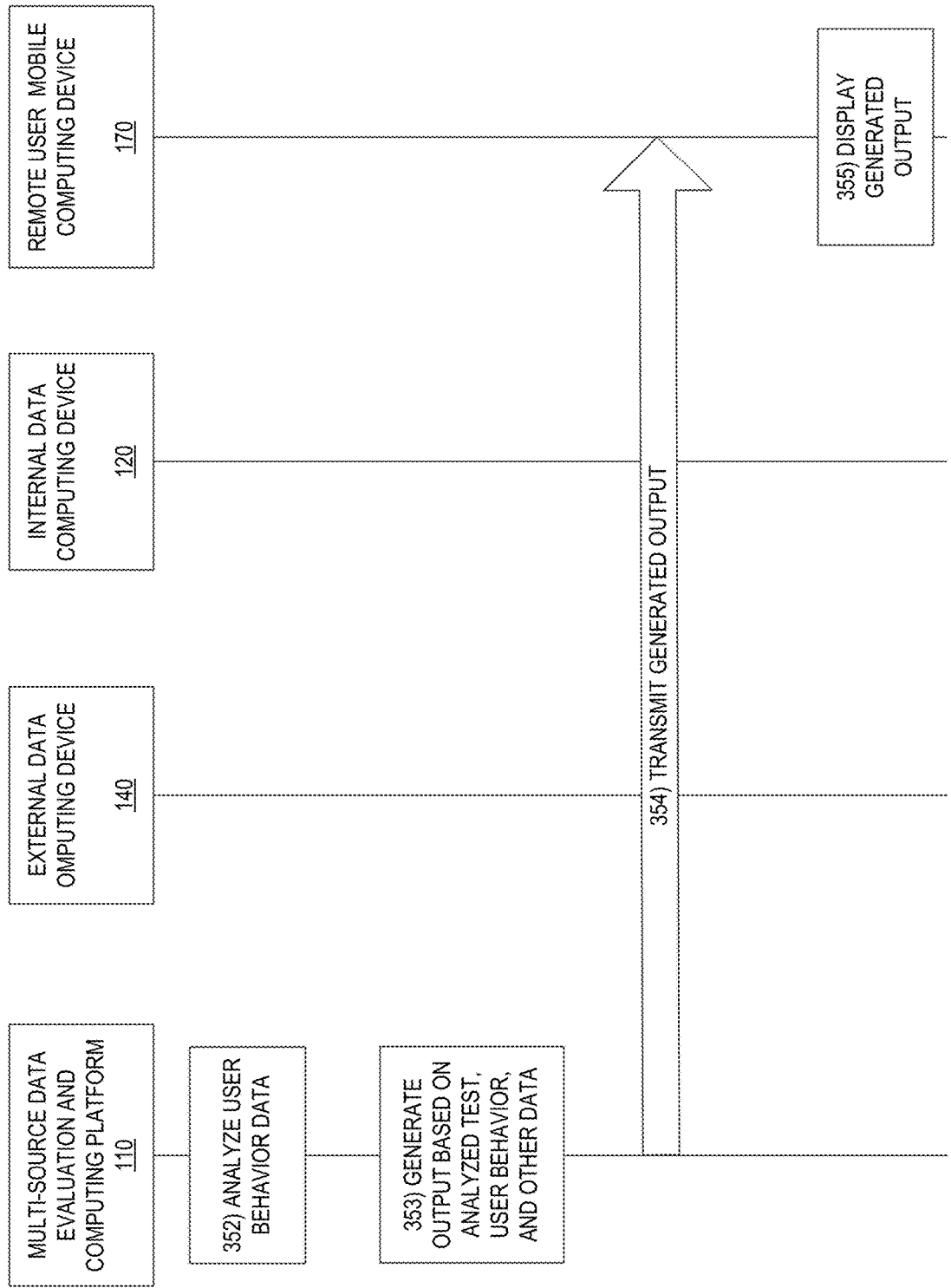

Referring to FIG. 3I, in step 352 the collected user behavior data may be analyzed by the multi-source data evaluation and control computing platform 110 to glean a user's behavior, habits, lifestyle choices, health/wellness status, etc. The collected user behavior data may be scanned for language or images which may be reflective of the user's behavior, habits, lifestyle choices, health/wellness status, etc. In particular, the user behavior data may be scanned to identify both risky and positive behavior on the part of the user. For example, the user behavior data may be scanned for certain language or certain images which describe or show the user engaging in risky or positive behavior. For instance, the user behavior data may be scanned for risky behavior such as smoking, skydiving, heavy drinking, unhealthy eating, use of illegal substances, dangerous driving, illegal activities, fighting, etc., as well as for positive behavior such as healthy eating, exercising, strong social connections, performing charity or volunteer work, learning a foreign language, taking a class, etc. The user behavior data may be further scanned to determine a quantity and a quality of a user's social connections and interactions. For example, to determine the quantity of social connections and interactions, the following information may be collected: a number of text messages or emails sent or received, a number of phone calls placed or received, a number of posts made, a number of posts in which the user is referenced, a number of photos posted, a number of photos containing images of the user, etc. To determine the quality of social connections and interactions the user behavior data may be further scanned to identify, for example, posts containing comments referring to the user's love or affection of another individual or posts referring the love or affection that another individual may have for the user. In some examples, one or more machine learning datasets may be used to analyze the user behavior data to glean the user's behavior, habits, lifestyle choices, health/wellness status, etc. The multi-source data evaluation and control computing platform 110 may use the analyzed user behavior data to generate a user behavior profile for the user. The user behavior profile may be composed of one or more user behavior scores. The user behavior scores may be calculated by weighting differently defined categories of the analyzed user behavior data to determine a series of component user behavior scores. The component scores may subsequently be aggregated to determine an overall user behavior score. The analyzed user behavior data may be categorized into various categories, such as images taken or posted by the user of the user engaging in risky behavior, posts posted by the user describ-ing the user engaging in risky behavior, emails/text messages/chats sent by the user describing the user engaging in risky behavior, images taken by another individual of the user engaging in risky behavior, posts posted by another individual describing the user engaging in risky behavior, emails/text messages/chats sent by another individual to the user describing the user engaging in risky behavior, images taken or posted by the user of the user engaging in positive behavior, posts posted by the user describing the user engaging in positive behavior, emails/text messages/chats sent by the user describing the user engaging in positive behavior, images taken by another individual of the user engaging in positive behavior, posts posted by another individual describing the user engaging in positive behavior, emails/text messages/chats sent by another individual to the user describing the user engaging in positive behavior, text messages sent by the user, text messages received by the user, emails sent by the user, emails received by the user, phone calls placed by the user, phone calls received by the user, chats initiated by the user, chats received by the user, posts posted by the user, posts in which the user is referenced, photos containing images of the user, emails/texts/chats/posts showing meaningful connections, images showing meaningful connections, etc. The number of instances for each of the different categories may be determined, for example, the number of phone calls placed by the user, the number of emails/text messages/chats sent by another individual to the user describing the user engaging in risky behavior, the number of images showing meaningful connections, etc. The series of component user behavior scores may be determined by multiplying the number of instances for each category of the analyzed user behavior data by a weighting factor associated with the category. The component user behavior scores may be aggregated to determine an overall user behavior score, and the user behavior profile may be defined by the component user behavior scores and the overall user behavior score. The user behavior data, scores and/or profile may be used together with the analyzed test data from step 341 to generate an output, such as an eligibility or pricing determination. In some instances, supplemental data may be collected from one or more additional sources, and the supplemental data may be used together with the user behavior data, scores, and/or profile and the test data to generate an output.

In step 353, an output may be generated based on the analysis of the sensor data collected for the interactive tests, the user behavior data, scores, and/or profile, and/or other data, such as the supplemental data. For instance, based on the comparison of the data to the one or more machine learning datasets, an output may be generated. In some examples, the generated output may be a life insurance policy having parameters generated based on the analysis of the data. Additionally or alternatively, a premium associated with the life insurance policy may also be generated as an output. In still other examples, a discount, rebate or other incentive may be generated as an output. For instance, if tobacco use is detected, the multi-source data evaluation and control system may generate an incentive such as a rebate if the user stops tobacco use and submits to a subsequent interactive condition evaluation test to confirm the tobacco use has stopped. In this case, subsequent collection of user behavior data may also occur and may be used as an additional means of corroborating that the user has stopped tobacco use. For example, user behavior data may be collected and scanned to confirm that no images, posts, comments, etc. exist showing or describing the user using tobacco since the date the user confirmed the tobacco use was stopped. If images, posts, comments, etc. are found showing or describing the user continuing tobacco use since the date the user confirmed the tobacco use was stopped, the multi-source data evaluation and control system may be unable to make a determination regarding whether the user is eligible for the incentive. In some instances, an adjustment on at least a component of pricing for a product or service, such as a behavior-based variable product, may be generated as an output. For example, when one or more of the user behavior scores meets a corresponding threshold value for that particular category of behavior and/or one or more of the test results meets a corresponding threshold value for that particular test, the multi-source data evaluation and control system may determine that the user is eligible for one or more products, incentives, discounts, rebates, or pricing adjustment etc.

In some examples, the multi-source data evaluation and control computing platform 110 may be unable to make a determination, based on the analysis of the test data and/or the user behavior data, regarding whether a premium, discount, incentive, pricing, etc. for a product may be offered to the user. This may occur, for example, when the results of one or more of the interactive condition evaluation tests is below a threshold value, when one or more of the component or overall user behavior scores is below a threshold value, or when a discrepancy is found between user provided information and the analyzed test or user behavior data. In such cases, the multi-source data evaluation and control computing platform 110 may generate output informing the user that additional information is necessary before a decision, e.g., an eligibility or pricing decision, may be made. For example, the output may be a notification informing the user that a formal underwriting process and/or a traditional medical examination may be necessary or that the user may need to contact the entity by phone, by mail, or via a website associated with the entity to provide additional information prior to a decision being made. Various other outputs may be generated without departing from the disclosure.

In step 354, the generated output may be transmitted to, for instance, the remote user mobile computing device 170. Additionally or alternatively, the generated output may be transmitted to another computing device, such as the first local computing device 150, the second local computing device 155, and/or the remote user computing device 175.

In step 355, the generated output may be displayed on the remote user mobile computing device 170. In some examples, displaying the generated output may include an option to accept the offered product or service, identified parameters, pricing adjustment, and the like. Selection of this option may bind the user and product or service provider. Accordingly, by executing the interactive condition evaluation tests, collecting and analyzing the user behavior data, and providing results to the multi-source data evaluation and control computing platform 110, the user may obtain the desired product or service or may have an appropriate adjustment made to an existing product or service based on the user's behavior and/or health/wellness status without submitting to a formal underwriting process, which may include a physical examination, and the like.

Figure 4:
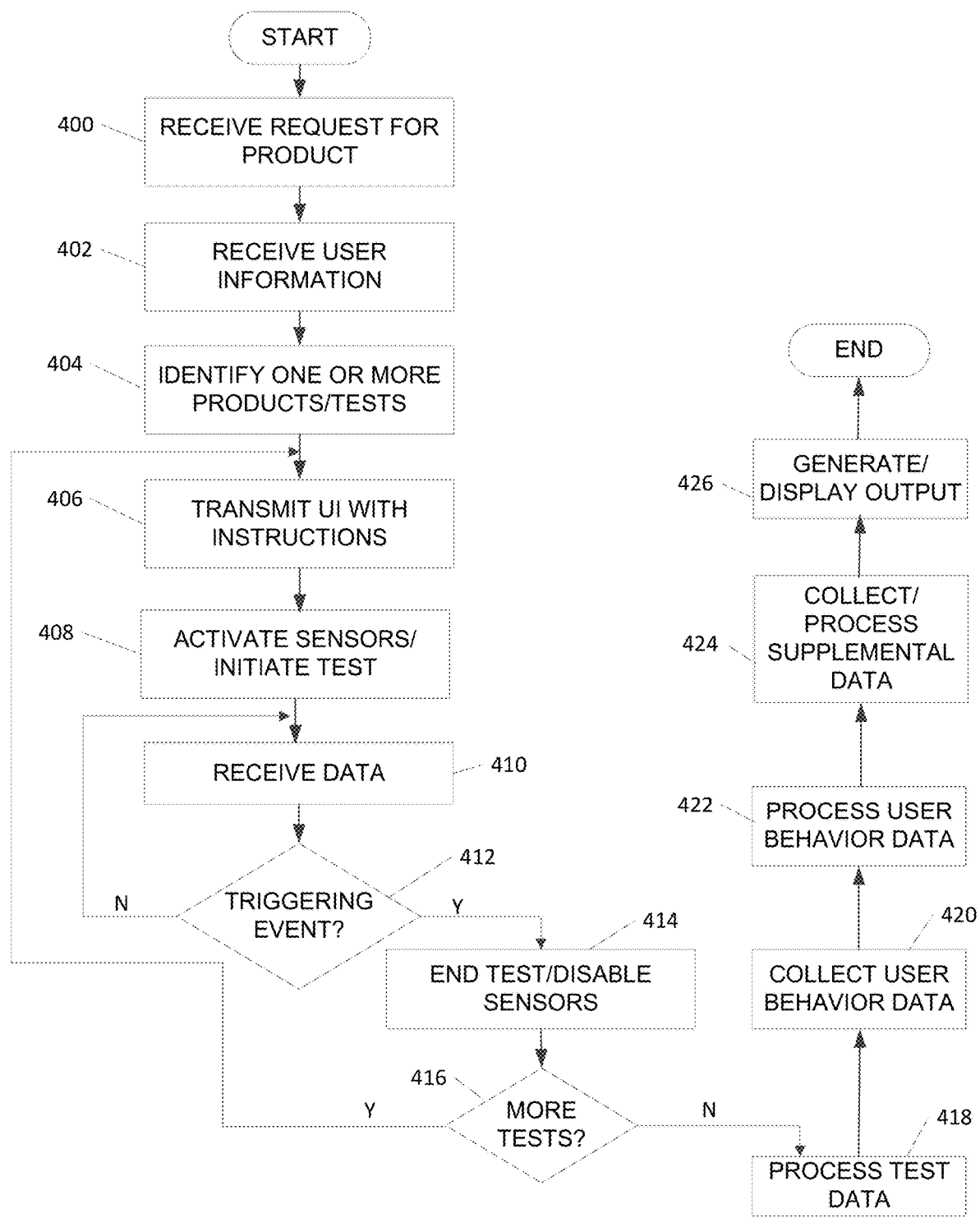
FIG. 4 illustrates one example flow chart illustrating an example method of performing a multi-source data evaluation and generating an output, according to one or more aspects described herein.

FIG. 4 illustrates one example process for generating and evaluating interactive condition evaluations tests and/or other data and collecting and analyzing social data, to generate an output according to one or more aspects described herein. The steps described with respect to FIG. 4 may be performed by one or more of the various devices described herein, such as the multi-source data evaluation and control computing platform 110, the interactive test generation multi-source data evaluation and control server 210, the remote user mobile computing device 170, and the like. In some examples, one or more of the processes or steps described may be performed in real-time or near real-time.

In step 400, a request for a product or service may be received. In some examples, the request may be received from a user computing device, such as the remote user mobile computing device 170. The request may be for an existing product or service. In some examples, the request may be automatically generated on a periodic basis, such as for an existing product or service.

In step 402, user information may be received from, for instance, the remote user mobile computing device 170. In some examples, the user information may include information requested by, for instance, the multi-source data evaluation and control computing platform 110 and may include information such as age, gender, location, email address, social media account information, other account information, authorization to collect information, and the like. Steps 400 and 402 may be optional in the instance where user eligibility is automatically determined without a user request.

In step 404, one or more products or services and corresponding interactive condition evaluation tests may be identified. For instance, the received user information may be used to identify one or more products for which the user may be eligible and that meet the request for the product or one or more existing products or services for the user. In the case where the user has one or more existing products or services, step 404 may be initiated automatically on a periodic basis (e.g., daily, weekly, monthly, on a predetermined schedule, etc.) to identify those products and services of the user which require revaluation for eligibility for pricing adjustments, incentives, discounts, rebates, etc. In this case, step 404 may be performed without the need to perform steps 400 to 402. When step 404 is initiated automatically on a periodic basis, the multi-source data evaluation and control computing platform 110 may identify the one or more existing products or services requiring reevaluation after determining that a predetermined time, associated with the periodic schedule, has elapsed since the product or service was last evaluated for eligibility or since the product or service was purchased. Based on the identified one or more products, one or more interactive condition evaluation tests may be identified to determine whether the user is eligible for the identified one or more products.

In step 406, a user interface including instructions for executing an interactive condition evaluation test of the identified one or more interactive condition evaluation tests may be generated and transmitted to, for instance, the remote user mobile computing device 170. In one example, the generated user interface may include a link to a mobile application related to an interactive condition evaluation test. The mobile application may generate and display, on the remote user mobile computing device 170, a user interface for executing the interactive condition evaluation test.

In step 408, an instruction or command may be transmitted to, for instance, the remote user mobile computing device 170 to activate one or more sensors associated with the interactive condition evaluation test and initiate the interactive condition evaluation test.

In step 410, data may be collected from one or more sensors, monitoring or usage devices, or the like, associated with the remote user mobile computing device 170. For instance, data from sensors associated with the interactive condition evaluation test being executed may be collected and/or transmitted to the multi-source data evaluation and control computing platform 110.

In step 412, a determination is made as to whether a triggering event has occurred. In some examples, a triggering event may include an indication that a test is complete, that one or more parameters or criteria of the test have been met, that a threshold amount of data has been received, or the like. If, in step 412, a triggering event has not occurred, the process may return to step 410 to continue collecting data.

If, in step 412, a triggering event has occurred, then in step 414, the interactive condition evaluation test may be terminated, for example, the multi-source data evaluation and control computing platform 110 may transmit an instruction, signal, or command to terminate the test and, in some examples, disable or deactivate one or more sensors activated for execution of the interactive condition evaluation test.

In step 416, a determination may be made as to whether there are additional tests identified for execution (e.g., a second or more tests identified in step 404). If so, the process may return to step 406 and may generate and transmit instructions for a second test, etc.

If, in step 416, a determination is made that there are no additional tests identified for execution, the collected sensor data may be processed in step 418. In some examples, the collected sensor data may be processed by itself. In other examples, the collected sensor data may be processed with other data, such as user behavior data and/or supplemental data from one or more other sources, after the other data is collected. Processing the sensor data may include comparing the sensor data to one or more machine learning datasets to detect a result of one or more of the interactive condition evaluation test and/or to predict or identify an output.

In step 420, one or more types of user behavior data to be collected may be identified based on the product or service for which the request in step 400 is received. The user behavior data of the identified type, such as social media posts and comments from social networking services, email messages, text messages, chats, images related thereto, phone calls, contacts, social media friends/connections, etc., may be collected (e.g., with appropriate user permission) from one or more sources, such as the external data computing device 140, the remote user mobile computing device 170, or other computing devices associated with the user or associated with another individual associated with the user.

In step 422 the collected user behavior data may be processed to glean a user's social behavior, habits, and lifestyle choices. For instance, the collected social data may be scanned for language and images which may indicate risky and/or positive behavior, habits, or lifestyle choices of the user. Processing the user behavior data may further include calculating one or more user behavior scores. In particular a series of component scores may be calculated for each category of user behavior data by multiplying the number of instances for the category by a weighted factor. The series of component user behavior scores may be aggregated to determine an overall behavior score. A user behavior profile may be generated comprising the component and overall user behavior scores. Processing the user behavior data may additionally include comparing the data to one or more machine learning datasets to make decisions regarding whether the scanned language and images indicate risky or positive behavior habits and/or and to predict or identify an output. In some instances, the collected user behavior data may be processed with other data, such as test data and/or supplemental data from one or more other sources, after the other data is collected.

In step 424, additional data may be collected and processed. For example, supplemental data, such as user information (e.g., names, addresses, ages, genders, email addresses, social media account information, other account information, and the like), demographic information, locality information, behavioral information (e.g., exercise habits, each habits, etc.), purchase habits or history, medical information, additional behavioral data collected by other sources, and the like may be collected. The collected supplemental data may be processed by comparing the data to one or more machine learning datasets to evaluate the data and/or to predict or identify an output. In some instances, the collected supplemental data may be processed with other data, such as test data and/or user behavior data, after the other data is collected.

In step 426, an output may be generated, based on the results of the interactive condition evaluation tests, the user behavior data, scores, and profile and/or the supplemental data. The output may be transmitted to and displayed, for example, via a display of the remote user mobile computing device 170. In some examples, the output may include an insurance product recommendation, a premium for an insurance product, a discount or other incentive, determination for, at least, a component of pricing for an insurance product, such as a behavior-based variable product, or the like. In some examples, the output may include a notification that a determination regarding whether an insurance product recommendation, a premium for an insurance product, a discount or other incentive, a pricing determination, etc. may be offered to the user could not be made based solely on the results of the interactive condition evaluation tests user behavior data, and/or the supplemental data. In this case, the output may indicate that additional information is needed from the user before a decision may be made.

Figure 5:
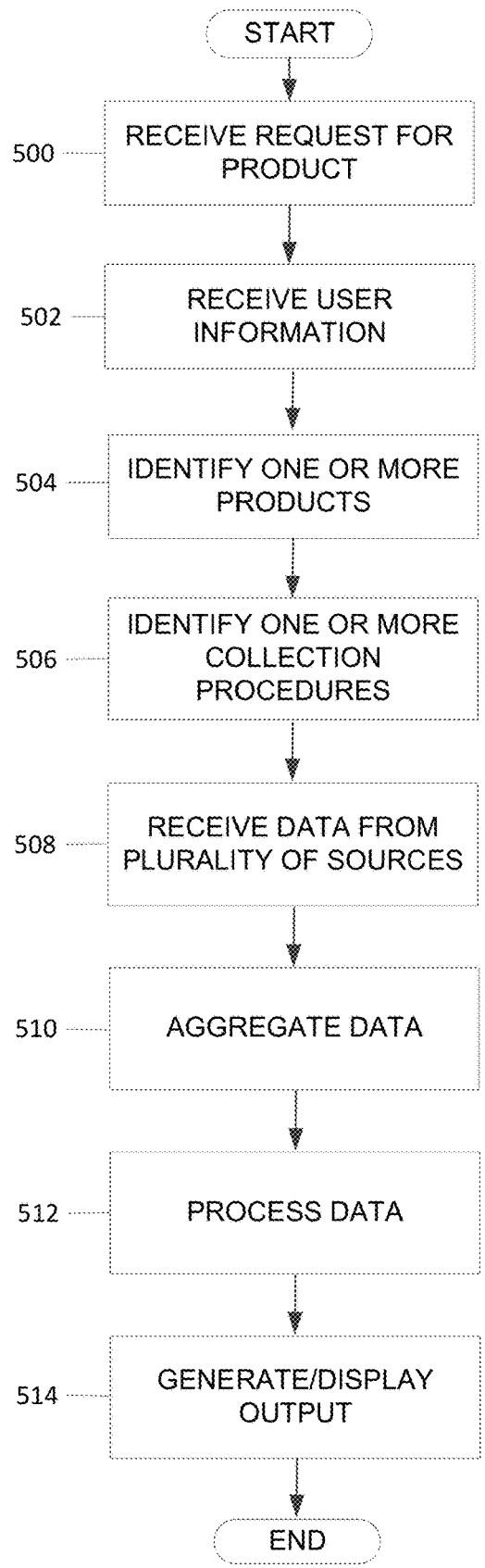
FIG. 5 illustrates one example flow chart illustrating an example method of performing a multi-source data evaluation and generating an output, according to one or more aspects described herein.

FIG. 5 illustrates one example process for aggregating data from disparate sources to generate an output according to one or more aspects described herein. The steps described with respect to FIG. 5 may be performed by one or more of the various devices described herein, such as the multi-source data evaluation and control computing platform 110, the multi-source data evaluation and control server 210, the remote user mobile computing device, and the like. In some examples, one or more of the processes or steps described may be performed in real-time or near real-time.

In step 500, a request for a product or service may be received. The request may be for an existing product or service of a user. In some examples, the request may be received from a user computing device, such as the remote user mobile computing device 170.

In step 502, user information may be received from, for instance, the remote user mobile computing device 170. In some examples, the user information may include information requested by, for instance, the multi-source data evaluation and control computing platform 110 and may include information such as age, gender, location, email address, social media account information, other account information, authorization to collect data, and the like. Steps 500 and 502 may be optional, such as in the instance where user eligibility is automatically determined without a user request.

In step 504, one or more products or services may be identified. For instance, the received user information may be used to identify one or more products or services for which the user may be eligible and that meet the request for the product/service. Alternatively, the received user information may be used to identify one or more existing products or services of the user. In the case where the user has one or more existing products or services, step 504 may be initiated automatically on a periodic basis (e.g., daily, weekly, monthly, on a predetermined schedule, etc.) to identify those products and services of the user which require revaluation for eligibility for pricing adjustments, incentives, discounts, rebates, etc. In this case, step 504 may be performed without the need to perform steps 500 to 502. When step 504 is initiated automatically on a periodic basis, the multi-source data evaluation and control computing platform 110 may identify the one or more existing products or services requiring reevaluation after determining that a predetermined time, associated with the periodic schedule, has elapsed since the product or service was last evaluated for eligibility or since the product or service was purchased.

In step 506, based on the products or services identified in step 504, one or one or more collection procedures may be identified for collecting the appropriate type of data which may be necessary to make a determination regarding the user's eligibility for the product/service or for pricing adjustments, incentives, discounts, rebates, etc. For example, based on the product or service identified in step 504, it may be determined that health-related data is necessary, or user behavior data is necessary, or data from various internal or external sources is necessary, or a combination thereof.

Accordingly, in some examples, the one or more collection procedures may include a procedure to collect health-related data from related to the user. In this case, based on the identified product or service, one or more interactive condition evaluation tests may be identified for execution at the user's device, such as the remote user mobile computing device 170. A request may be sent to the user's device, e.g., the remote user mobile computing device, to perform the collection procedure. The request may include user interfaces and instructions for executing the one or more interactive condition evaluation tests. The instructions may indicate that the device, e.g., the remote user mobile computing device 170, should activate one or more sensors associated with the device to collect data during execution of the interactive condition evaluation tests. This collection procedure may be similar to that described in steps 325 to 332 in FIGS. 3D-3E.

In some examples, the one or more collections procedures may include a procedure to collect user behavior data. In this case, based on the identified product or service, one or more types of user behavior may be identified to be collected by the user's device, such as the remote user mobile computing device 170. The one or more types of user behavior data may include social media posts and comments from social networking services, email messages, text messages, chats, images related thereto, phone calls, contacts, social media friends/connections, etc. The user behavior data may additionally include data associated with movement of the user's device, such as step count data or other activity data, how often the device is in motion, the type of motion or speed (e.g., walking vs. driving), types of applications often executed on the mobile device, and the like. The user behavior data may include other types of data described throughout the disclosure. A request may be sent to the user's device, such as the remote user mobile computing device 170, to perform the collection procedure. The request may include instructions for collecting the user behavior data. The instructions may indicate the identified type of user behavior data to be collected, the location of the data, a time range associated with the data to be collected (i.e., collect social media posts from the last month or the last year, etc.), a size limit, or the like. This collection procedure may be similar to that described in steps 342 to 348 in FIGS. 3G to 3H.

In some examples, the one or more collection procedures may include a procedure to collect data from sources internal to an entity. In this case, a request may be sent to one or more internal sources, such as the internal data computing device 120, to perform the collection procedure. The request may include instructions to collect data associated with a user, such as age, gender, location, whether the user is a homeowner, marital status, insurance history, claim history, driving behaviors, accident histories and associated damages/costs, and the like.

In some examples, the one or more collection procedures may include a procedure to collect data from one or more external sources. In this case, a request may be sent to one or more external sources, such as the external data computing device 140, to perform the collection procedure. The request may include instructions to collect data associated with the user, such as medical/prescription history, travel history, consumer data such as transaction or purchase history, behavioral information (e.g., gym membership, gym usage, spa membership, spa usage, and the like), as well as other external data. In some examples, the data to be collected may include social data related to users, such as social media posts, email messages, text messages, chats, images related thereto, phone calls, contacts, social media friends and/or connections, etc. In some examples, the device from which the data collection is requested, e.g., the external data computing device 140, is a computing device of an individual associated with the user (e.g., a friend, connection, relative, individual having a device connected to a device of the user, etc.) and participating in a service provided by the multi-source data evaluation and control system. In some examples, the external data computing device 140 is a computing device of an external service provider which collects and analyzes social data.

Various other types of data may be collected from the above-mentioned devices or from one or more other devices. At least some data collected pursuant to the collection procedures may be collected with permission of the user.

In step 508, the data collected in accordance with the one or more identified collection procedures may be received from one or more sources. For example, test data and or user behavior data may be received from the remote user mobile computing device 170, internal data may be received from the internal data computing device 120, and/or external data may be received from the external data computing device 140. Various other types of data may be received from the above-mentioned devices or from one or more other devices.

In step 510, the received data may be aggregated and, in step 512, the data may be processed to determine whether a user is eligible for the one or more products identified, to determine a discount or incentive, to determine, at least, a component of pricing for one or more products, such as a behavior-based variable product, etc. In some examples, processing the data may include using one or more machine learning datasets to evaluate the data for generating an output, such as an eligibility or pricing determination for a product.

In step 514, the output may be generated and/or displayed, for instance, on a user computing device.

Figure 6:
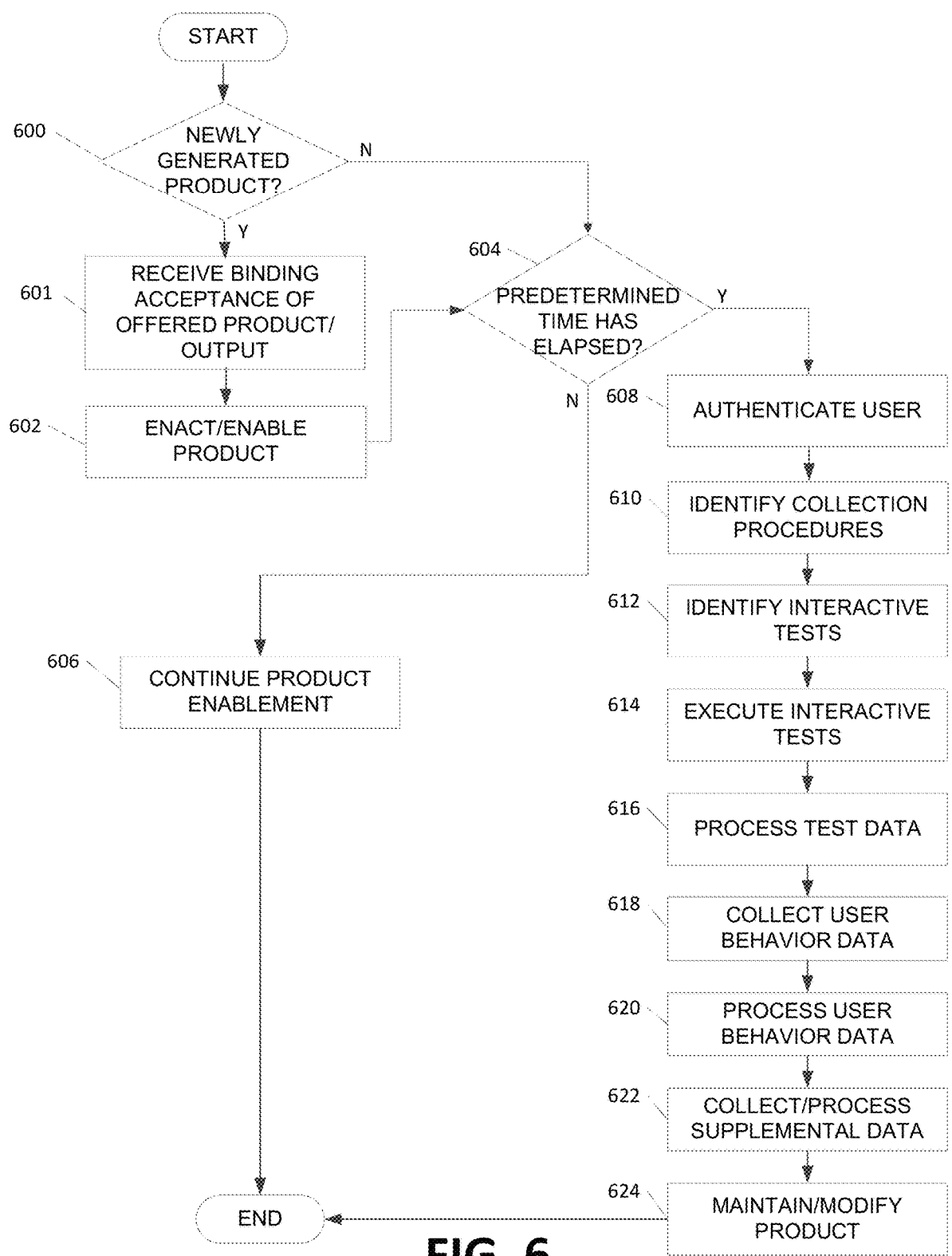
FIG. 6 illustrates one example flow chart illustrating an example method of performing a multi-source data evaluation using additional interactive condition evaluation tests and generating an output, according to one or more aspects described herein.

FIG. 6 illustrates one example process for renewing or adjusting pricing for a product by collecting additional data related to the user, such as data collected from one or more interactive condition evaluation tests, collected user behavior data, and/or collected supplemental data, according to one or more aspects described herein. The steps described with respect to FIG. 6 may be performed by one or more of the various devices described herein, such as the multi-source data evaluation and control computing platform 110, the multi-source data evaluation and control server 210, the remote user mobile computing device 170, and the like. In some examples, one or more of the processes or steps described may be performed in real-time or near real-time.

In step 600, a determination may be made as to whether a generated output relates to a newly offered product for a user or to an existing product of the user's. If the product is newly offered, the process may proceed to step 601, otherwise the process may proceed to step 604.

In step 601, a binding acceptance of the offered product or generated output may be received. In some examples, upon generating and displaying an output to a user, the user may have an option to select to accept an offer associated with the output. In some arrangements, accepting the offer may be a binding agreement and, for instance, may be performed without conventional underwriting processes.

In step 602, based on the binding acceptance, the product or generated output may be enabled or enacted. For instance, if the generated output is an insurance policy, acceptance of the binding offer may cause the policy to go into effect.

In step 604, a determination may be made as to whether a predetermined time period has elapsed. For example, the selected product or output may be enacted for a predetermined time period or term. Upon expiration of that term, the product may be cancelled if it is not renewed. Accordingly, in advance of the product being cancelled, and after a predetermined time (e.g., a predetermined time less than the term of the product), the system may offer the user an option to renew. Accordingly, the system may determine whether the predetermined time period less than the term of the product has elapsed. When the product is an existing product, the predetermined time period may relate to a predetermined time at which the user's behavior, habits, lifestyle, health/wellness, etc. may be reevaluated for a determination regarding whether pricing may be adjusted for at least a component of the product, such as a variable pricing component of a behavior-based variable product. Pricing may be adjusted on a periodic basis, such as daily, weekly, monthly, etc., on a predetermined schedule, or upon a user request. If the predetermined time period has elapsed, the process may proceed to step 608. If the predetermined time period has not elapsed, process may proceed to step 606, where the product may remain enabled or enacted at which point the process may end or return to step 600 to again determine whether the predetermined time period has elapsed.

If, in step 604, the predetermined time period has elapsed, the user may renew the product or the user's behavior, habits, lifestyle, health/wellness, etc. may be reevaluated for possible pricing adjustment of the product.

In step 608, the user may be authenticated to the system. For instance, a notification may be transmitted to the user requesting the user to login to the system for renewal. In some examples, logging in for renewal may include determining whether user authenticating credentials match pre-stored user authenticating credentials. In some examples, credentials may include username and password, biometric data such as fingerprint, iris scan, facial recognition, and the like.

In step 610, based on the product from step 600, one or more collection procedures may be identified to collect data necessary to make a determination regarding whether the user is eligible to renew the product, one or more parameters of a renewal, whether pricing may be adjusted, and the like. For example, based on the product, an interactive condition evaluation test collection procedure for collecting health-related data, a user behavior data collection procedure for collecting lifestyle-related data may be identified, and a supplemental data collection procedure for collecting additional data may be identified.

In step 612, the interactive condition evaluation test collection procedure may identify one or more interactive condition evaluation tests to be executed. Similar to other aspects described herein, the interactive condition evaluation tests may be identified based on user information, a current product, and the like. A request may be sent to a computing device of the user, e.g., the remote user mobile computing device 170, instructing the device to execute the one or more interactive condition evaluation tests.

In step 614, the one or more interactive condition evaluation tests may be executed via a computing device of the user (e.g., the remote user mobile computing device 170) and test data may be collected during test execution In step 616, the test data may be processed, for instance, using one or more machine learning datasets, to determine test results. In some examples, steps 612 through 616 may be optional. For example, for an eligibility determination for pricing or adjustment thereof of an existing product or service, e.g., a behavior-based variable product, it may not be necessary to collect test data. In such cases, collection and processing of only user behavior data or other data, e.g., supplemental data, may be necessary to make the determination.

In step 618, the user behavior data collection procedure may identify one or more types of user behavior data to be collected based on the product identified in step 600. A request may be sent to a computing device of the user, e.g., the remote user mobile computing device 170, instructing the device to collect the identified types of user behavior data. The remote user mobile computing device 170 may collect the identified types of user behavior data, In step 620, the collected user behavior data may be processed to glean the user's behaviors, habits, lifestyle choices, health/wellness status. User behavior scores may be calculated and used to generate a user behavior profile for the user. The user behavior data, scores, and profile may be processed using one or more machine learning datasets.

In step 622, supplemental data collection procedure may identify additional data to be collected, such as supplemental data, may be collected and processed. The additional data may be processed using one or more machine learning datasets.

In step 624, based on the processed test data, user behavior data, and/or supplemental data, an output may be generated and displayed to the user. In some examples, the output may include an offer or recommendation to maintain or renew the product currently enabled or to modify the product (e.g., obtain a different product, modify one or more parameters of the product, and the like). In some examples, the output may include a determination to adjust at least a component of pricing for the product, such as a variable pricing component for a behavior-based variable product. Alternatively, the output may include a notification indicating that additional information is needed before a decision may be made regarding an offer or recommendation to maintain, renew, modify, or adjust pricing of the product. For example, if one or more of the user behavior scores meets a corresponding threshold value for the particular type of user behavior score or if one or more of the test results meets a corresponding threshold value for the particular type of test, a determination may be made to adjust at least a component of pricing for the product. The determination may be output to the user, such as via a display of the user's device, e.g., the remote user mobile computing device 170. Alternatively, if one or more of the user behavior scores does not meet a corresponding threshold value for the particular type of user behavior score or if at least one of the test results does not meet a corresponding threshold value for the particular type of test, eligibility for the pricing adjustment may be uncertain and a notification indicating that additional information is needed may be provided to the user, such as via a display of the user's device, e.g., the remote user mobile computing device 170.

Figure 7:
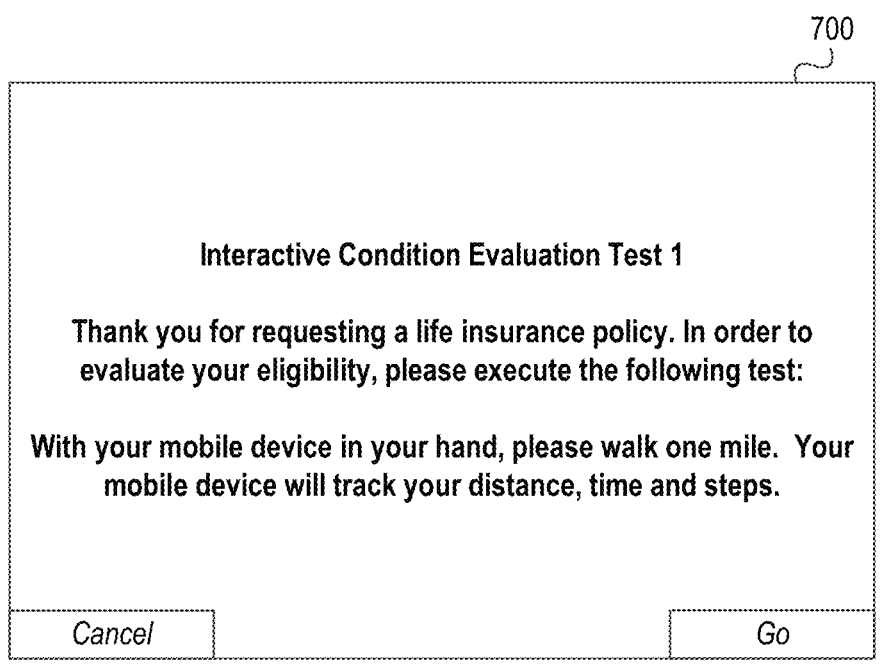
FIG. 7 illustrates one example user interface for executing an interactive condition evaluation test, according to one or more aspects described herein.

FIG. 7 illustrates one example user interface that may be generated and transmitted to a mobile device of a user. The user interface 700 may include identification of a first test, instructions for performing the first test, and the like. The user may initiate the test by selecting "GO" or other option.

Figure 8A:
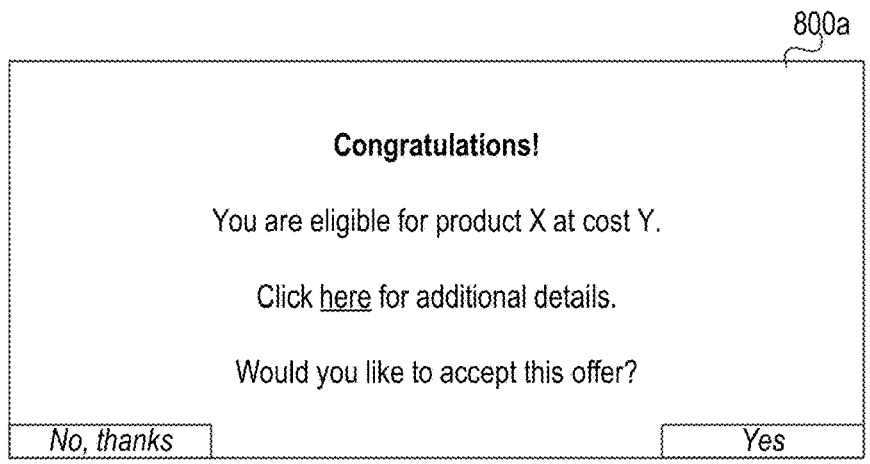
FIGS. 8A to 8C illustrate example user interfaces for displaying a generated output, according to one or more aspects described herein.
Figure 8B:
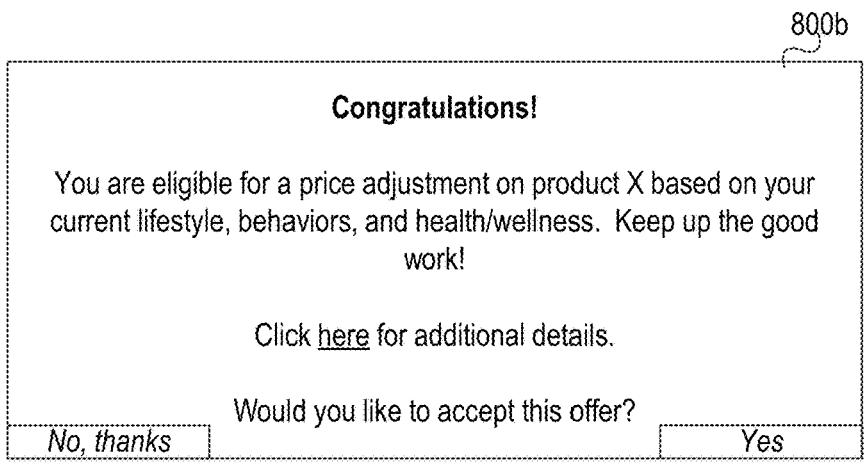
Figure 8C:
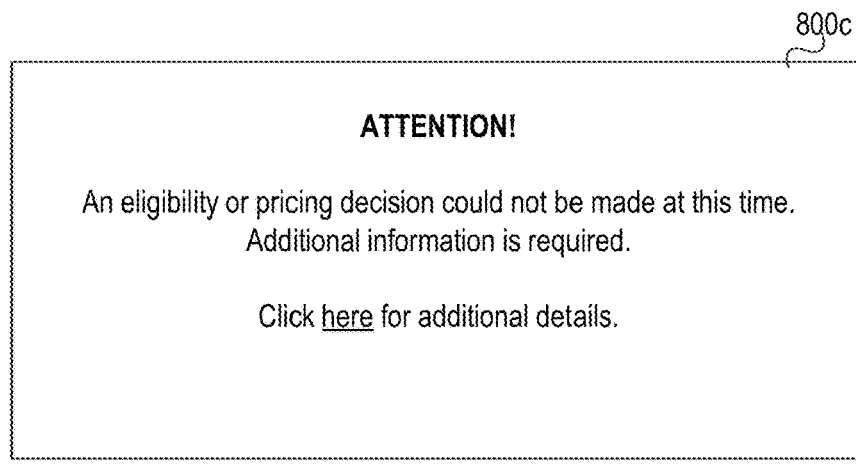

FIGS. 8A to 8C illustrate example user interfaces providing a generated output. Referring to FIG. 8A, the interface 800a may include an indication of the product for which the user is eligible or the product being offered, as well as a cost associated with the product. In some examples, a link may be provided to additional information, parameters, term, conditions, and the like. The interface 800a may further include an option to accept the offer. Acceptance of the offer may bind the user in real-time, in at least some examples.

Referring to FIG. 8B, the interface 800b may include a notification of eligibility for a price adjustment for an existing product based on the user's lifestyle, behaviors, habits, health/wellness, etc. In some examples, a link may be provided to additional information about the adjustment. The interface 800b may further include an option to accept the adjustment. In some examples, the interface 800b may include a notification for the price adjustment, as per previously agreed upon terms, without requiring user approval.

Referring to FIG. 8C, the interface 800c may include a notification indicating that additional information is necessary prior to a decision being made. In some examples, a link may be provided to provide the user with additional details about the additional information needed to proceed with determination for eligibility, price adjustment, etc.

FIG. 9 illustrates a block diagram of a computing device (or system) 901 in a computer system 900 that may be used according to one or more illustrative embodiments of the disclosure. The computing device 901 may have a processor 903 for controlling overall operation of the computing device 901 and its associated components, including RAM 905, ROM 907, input/output module 909, and memory 915. The computing device 901, along with one or more additional devices (e.g., terminals 950 and 951, security and integration hardware 960) may correspond to any of multiple systems or devices, such as a user personal mobile computing device, computing platform, or a computer server, configured as described herein for collecting data, identifying and executing one or more interactive condition evaluation tests, evaluating the data, generating outputs, and the like.

The input/output (I/O) 909 may include a microphone, keypad, touch screen, and/or stylus through which a user of the computing device 901 may provide input, and may also include one or more of a speaker for providing audio output and a video display device for providing textual, audiovisual and/or graphical output.

Software may be stored within the memory 915 and/or storage to provide instructions to the processor 903 for enabling the computing device 901 to perform various actions. For example, the memory 915 may store software used by the computing device 901, such as an operating system 917, application programs 919, and an associated internal database 921. The various hardware memory units in the memory 915 may include volatile and nonvolatile, removable and non-removable media implemented in any method or technology for storage of information such as computer readable instructions, data structures, program modules or other data. Certain devices/systems within the multi-source data evaluation and control system may have minimum hardware requirements in order to support sufficient storage capacity, analysis capacity, network communication, etc. For instance, in some embodiments, one or more nonvolatile hardware memory units having a minimum size (e.g., at least 1 gigabyte (GB), 2 GB, 5 GB, etc.), and/or one or more volatile hardware memory units having a minimum size (e.g., 256 megabytes (MB), 512 MB, 1 GB, etc.) may be used in the computing device 901 (e.g., a mobile computing device 901, an multi-source data evaluation and control server 901, an external server 901, etc.), in order to store and execute a multi-source data evaluation and control software application, execute tests, collect and analyze data, generate outputs, generate recommendations and/or incentives, etc. The memory 915 also may include one or more physical persistent memory devices and/or one or more non-persistent memory devices. The memory 915 may include, but is not limited to, random access memory (RAM) 905, read only memory (ROM) 907, electronically erasable programmable read only memory (EEPROM), flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by the processor 903.

The processor 903 may include a single central processing unit (CPU), which may be a single-core or multi-core processor (e.g., dual-core, quad-core, etc.), or may include multiple CPUs. The processor(s) 903 may have various bit sizes (e.g., 16-bit, 32-bit, 64-bit, 96-bit, 128-bit, etc.) and various processor speeds (ranging from 100 MHz to 5 GHz or faster). The processor(s) 903 and its associated components may allow the computing device 901 to execute a series of computer-readable instructions, for example, to identify interactive condition evaluation tests, execute tests, collect and analyze data, generate outputs, and the like.

The computing device 901 (e.g., a mobile computing device, computing platform, server, external server, etc.) may operate in a networked environment, e.g., the computer system 900, supporting connections to one or more remote computers, such as terminals 950 and 951. The terminals 950 and 951 may be personal computers, servers (e.g., web servers, database servers), or mobile communication devices (e.g., mobile phones, portable computing devices, on-board vehicle-based computing systems, and the like), and may include some or all of the elements described above with respect to the computing device 901. The network connections depicted in FIG. 9 include a local area network (LAN) 925 and a wide area network (WAN) 929, and a wireless telecommunications network 933, but may also include other networks. When used in a LAN networking environment, the computing device 901 may be connected to the LAN 925 through a network interface or adapter 923. When used in a WAN networking environment, the computing device 901 may include a modem 927 or other means for establishing communications over the WAN 929, such as network 931 (e.g., the Internet). When used in a wireless telecommunications network 933, the computing device 901 may include one or more transceivers, digital signal processors, and additional circuitry and software for communicating with wireless computing devices 940 (e.g., mobile phones, portable computing devices, on-board vehicle-based computing systems, etc.) via one or more network devices 935 (e.g., base transceiver stations) in the wireless telecommunications network 933.

Also illustrated in FIG. 9 is a security and integration layer 960, through which communications may be sent and managed between the computing device 901 (e.g., a user's personal mobile device, an multi-source data evaluation and control computing platform or server, etc.) and the remote devices (the terminals 950 and 951) and remote networks (the LAN 925, the WAN 929, and the wireless telecommunications network 933). The security and integration layer 960 may comprise one or more separate computing devices, such as web servers, authentication servers, and/or various networking components (e.g., firewalls, routers, gateways, load balancers, etc.), having some or all of the elements described above with respect to the computing device 901. As an example, the security and integration layer 960 of a mobile computing device, computing platform, or a server operated by an insurance provider, financial institution, governmental entity, or other organization, may comprise a set of web application servers configured to use secure protocols and to insulate the server, e.g., the computing device 901, from external devices, e.g., the terminals 950 and 951. In some cases, the security and integration layer 960 may correspond to a set of dedicated hardware and/or software operating at the same physical location and under the control of same entities as the computing device 901. For example, the security and integration layer 960 may correspond to one or more dedicated web servers and network hardware in an organizational datacenter or in a cloud infrastructure supporting a cloud-based multi-source data evaluation and control system. In other examples, the security and integration layer 960 may correspond to separate hardware and software components which may be operated at a separate physical location and/or by a separate entity.

As discussed below, the data transferred to and from various devices in the computer system 900 may include secure and sensitive data, such as device usage data, application usage data, medical or personal information, test result data, and the like. Therefore, it may be desirable to protect transmissions of such data by using secure network protocols and encryption, and also to protect the integrity of the data when stored on in a database or other storage in a mobile device, multi-source data evaluation and control computing platform, or server and other computing devices in the computer system 900, by using the security and integration layer 960 to authenticate users and restrict access to unknown or unauthorized users. In various implementations, security and integration layer 960 may provide, for example, a file-based integration scheme or a service-based integration scheme for transmitting data between the various devices in the computer system 900. Data may be transmitted through the security and integration layer 960, using various network communication protocols. Secure data transmission protocols and/or encryption may be used in file transfers to protect to integrity of the driving data, for example, File Transfer Protocol (FTP), Secure File Transfer Protocol (SFTP), and/or Pretty Good Privacy (PGP) encryption. In other examples, one or more web services may be implemented within the computing device 901 in the computer system 900 and/or the security and integration layer 960. The web services may be accessed by authorized external devices and users to support input, extraction, and manipulation of the data (e.g., device usage data, location data, vehicle data, etc.) between the computing device 901 in the computer system 900. Web services built to support the computer system 900 may be cross-domain and/or cross-platform, and may be built for enterprise use. Such web services may be developed in accordance with various web service standards, such as the Web Service Interoperability (WS-I) guidelines. In some examples, a movement data and/or driving data web service may be implemented in the security and integration layer 960 using the Secure Sockets Layer (SSL) or Transport Layer Security (TLS) protocol to provide secure connections between servers, e.g., computing device 901, and various clients, e.g., terminals 950 and 951 (e.g., mobile devices, data analysis servers, etc.). SSL or TLS may use HTTP or HTTPS to provide authentication and confidentiality. In other examples, such web services may be implemented using the WS-Security standard, which provides for secure SOAP messages using XML encryption. In still other examples, the security and integration layer 960 may include specialized hardware for providing secure web services. For example, secure network appliances in the security and integration layer 960 may include built-in features such as hardware-accelerated SSL and HTTPS, WS-Security, and firewalls. Such specialized hardware may be installed and configured in the security and integration layer 960 in front of the web servers, so that any external devices may communicate directly with the specialized hardware.

Although not shown in FIG. 9, various elements within the memory 915 or other components in the system 900, may include one or more caches, for example, CPU caches used by the processor 903, page caches used by the operating system 917, disk caches of a hard drive, and/or database caches used to cache content from the database 921. For embodiments including a CPU cache, the CPU cache may be used by one or more processors in the processor 903 to reduce memory latency and access time. In such examples, the processor 903 may retrieve data from or write data to the CPU cache rather than reading/writing to the memory 915, which may improve the speed of these operations. In some examples, a database cache may be created in which certain data from the database 921 (e.g., interactive condition evaluation test result database, internal data database, external data database, etc.) is cached in a separate smaller database on an application server separate from the database server. For instance, in a multi-tiered application, a database cache on an application server can reduce data retrieval and data manipulation time by not needing to communicate over a network with a back-end database server. These types of caches and others may be included in various embodiments, and may provide potential advantages in certain implementations of performing functions describes herein.

It will be appreciated that the network connections shown are illustrative and other means of establishing a communications link between the computers may be used. The existence of any of various network protocols such as TCP/IP, Ethernet, FTP, HTTP and the like, and of various wireless communication technologies such as LTE, GSM, CDMA, WiFi, and WiMAX, is presumed, and the various computer devices and system components described herein may be configured to communicate using any of these network protocols or technologies.

Additionally, one or more application programs 919 may be used by the computing device 901 within the computer system 900 (e.g., software applications, etc.), including computer executable instructions for identifying one or more products, identifying one or more interactive condition evaluation tests, executing interactive condition evaluation tests, collecting data, analyzing data, and the like, as described herein.

As discussed herein, various examples for generating an output based on different types of data from different sources are described. In some examples, machine learning may be used to generate one or more outputs. Using data from various different sources, as well as different types of data, may provide more accurate predictions of risk, mortality, and the like, in order to generate and offer outputs that are more closely tailored to a user's needs.

Further, using the various types of data, as well as machine learning, may allow an entity generating an output to better align pricing with a determined risk. In conventional systems, it may take several years to evaluate outputs, such as a determined risk for a particular user, a predicted mortality, or the like. By processing great volumes of data to generate machine learning datasets, validation of risk predictions or assumptions, and the like may be performed much more quickly which ultimately may allow for pricing of products (e.g., insurance policies, and the like) at a more granular level.

As discussed, one or more interactive condition evaluation tests may be used to collect data associated with a user, assess conditions of the user, the resulting test data, together with other data, such as user behavior data and/or supplemental data, may be used to determine whether a user is eligible for a product, a discount, an incentive, a pricing adjustment, etc. and/or to generate an output (e.g., an insurance policy to offer, a premium for an insurance policy, a discount or incentive, or the like). Below are several example interactive condition evaluation tests that may be used with one or more arrangements described herein. Various other tests may be used without departing from the disclosure and nothing in the examples below should be viewed as limiting the interactive condition evaluation tests to only these examples.

In one example, an interactive condition evaluation test may include evaluating mobility of a user. Accordingly, the multi-source data evaluation and control computing platform 110 may generate a user interface including instructions for executing a mobility test using a mobile device of the user. The user may receive the interface which may be displayed on the mobile device. In some examples, the test may include instructing a user to walk, run, jog, or the like, a predetermined distance. Sensors within the mobile device may track the distance walked, time for walking the distance, pace of the user, and the like. In some examples, data related to heart rate of the user, pulse of the user, and the like, may also be collected by one or more sensors in the mobile device. This information may then be transmitted to the multi-source data evaluation and control computing platform 110 for processing and analysis.

In another example, a user may be instructed to walk, run, jog, or the like, on a treadmill for a predetermined time, at a predetermined pace, or the like, while carrying the user's mobile device. Sensors within the device may detect and/or collect data associated with performance of the test, heart rate, pulse, and the like, and this information may be transmitted to the multi-source data evaluation and control computing platform 110 for processing and analysis.

In some arrangements, for either of the above-described example interactive tests, video may be captured of the user while performing the test. This video may be further evaluated to determine a gait of user, how easily the user managed the interactive test, or the like.

In other example interactive tests, a user may be instructed to perform one or more other physical functions (e.g., outside of walking, running or the like). For instance, a user may be requested to hold his or her arms in front of his or her body for as long as possible while holding the mobile device. One or more sensors within the mobile device may collect data associated with a position of the mobile device, time in a particular position, and the like, and this information may be transmitted to the multi-source data evaluation and control computing platform 110 for processing and analysis.

In some examples, similar physical tests may be performed with a user's legs (e.g., sit in chair and extend legs).

In some examples, one or more interactive tests may test a reflex of a user. For instance, an image may be displayed on a mobile device of a user with instructions to touch one or more icons indicating a certain item (e.g., a plurality of icons are displayed, touch or select all that are a particular object). The sensors and/or other mobile device components may detect not only how many correct answers the user provided but also how quickly the user was able to respond (e.g., how quickly the user could touch the screen). This data may then be transmitted to the multi-source data evaluation and control computing platform 110 for processing an analysis.

In another example interactive condition evaluation test for reflexes, the user may be instructed to touch a display of the mobile device as quickly as possible upon seeing a particular prompt. The mobile device may then collect data associated with how quickly the user touched the display and may transmit that data for processing and analysis.

Additional interactive condition evaluation tests may be directed to evaluating a user's recall. For instance, a user may be provided with a list of words that they may view for a predetermined time period. After the time period expires, the user may be requested to input as many words as he or she can remember. The words may be input via a keyboard (e.g., virtual or physical) or spoken.

In some examples, one or more interactive condition evaluation tests may be used to evaluate a lung capacity or respiration of a user. For instance, a tobacco user may have a reduced lung capacity, increased respiration rate, or the like. Accordingly, one or more interactive condition evaluation tests may include having a user exhale onto a mobile device and one or more sensors may be detect a number of exhalations, a velocity of the breath, a rate of exhalations, and the like. In some examples, the user may exhale onto a microphone of the mobile device and the audio received may be processed to determine a strength of exhale, number of exhalations, and the like. In some examples, one or more test may request a user to exhale for a predetermined amount of time while positioned a predetermined distance from the mobile device. This information may be transmitted to the multi-source data evaluation and control computing platform 110 for processing and analysis.

In some examples, one or more interactive condition evaluation tests may include monitoring sleep habits of a user. This data may then be transmitted for processing and analysis.

In some examples, one or more interactive condition evaluation tests may including requesting a user to capture one or more images of particular body parts, or the like. For instance, images of the user may be used to determine height, weight, overall health appearance, and the like. In some examples, the user may be requested to submit particular images. For instance, a close up image of an eye of a user may be used to determine one or more health issues, such as coronary disease, hypertension, diabetes, and the like.

Various other interactive condition evaluation tests may be provided using data collected from one or more sensors associated with the user's mobile device, such as a body mass index (BMI) measurement test, a body composition test, a visceral fat measurement test, a maximum oxygen consumption ($VO_2$ max) test, a metabolic rate test, a blood pressure measurement test, a heart rate measurement test, a test to detect a user's smoking status, and the like.

In some examples, the system may generate a plurality of tests for execution. A user may, in some examples, complete some or all of the tests. If the user completes fewer than all of the tests, the output generated may be impacted by completion of fewer than all of the identified tests (e.g., output may include a higher premium for a policy than a user completing all tests, discount or incentive may be different from a user who completed all tests, or the like).

Although various aspects described herein are described as being executed by a mobile device of a user, a mobile device may, in some examples, include a wearable device, such as a fitness tracker. One or more tests may be executed via the fitness tracker, data may be collected and transmitted, and the like. In some examples, data from a fitness tracker or other wearable device may be used in combination with other data (e.g., may be used as data from an external source, collected, aggregated and processed, as discussed herein).

Data from sources other than the interactive condition evaluation tests may also be used, as discussed herein. For instance, user behavior data collected from one or more devices, data from internal sources, and/or external sources may be used to evaluate risk, generate outputs, provide offers, and the like.

For instance, in some examples, data associated with usage of a mobile device may be collected and used in analyzing eligibility, generating outputs, and the like. For instance, types of applications accessed by a user, how often applications are accessed, and the like, may be collected and used in the analysis. For example, if a user executes one or more health or fitness applications on a mobile device, that may indicate a healthy lifestyle. Alternatively, if the mobile device is often used for streaming video, that may indicated a more sedentary lifestyle. These factors may be used to evaluate eligibility, determine an output, or the like.

As discussed herein, various types of internal data may be collected and used in making various output determinations. For instance, if the entity implementing the system is an insurance provider, data associated with home insurance, auto insurance, life insurance, and the like may be used. In some examples, historical data such as claims data, and the like, may be used in generating one or more machine learning datasets. Data associated with a particular user requesting a product may also be extracted and used to generate an output. For example, user claim history, vehicle operational data or driving behaviors (e.g., as collected from a vehicle of the user, mobile device of the user, or the like), may be used.

As also discussed herein, various types of external data may be collected and used in making various output determinations. In some examples, the external data may be received from one or more sources external to an entity implementing the system. The external sources may include publicly available information, anonymous information, information collected with permission of the user, and the like. Some examples of external data are provided below. However, various other types of external data may be collected and used without departing from the disclosure and the examples below should not be viewed as limiting external data to only these types of data.

In some examples, consumer data such as transaction data and the like may be used. For instance, data collected via a loyalty program at grocery stores, department stores, and the like, may be used to evaluate a lifestyle of user. Data such as types of purchases made, locations of purchase, frequency of purchase, amount of purchase, and the like may be considered. In some examples, purchases made at a grocery store (e.g., healthy foods, cigarettes, alcohol, or the like) may be collected and evaluated to generate one or more outputs.

In some examples, external data such as medical information of the user may be collected and used in the analysis. This data may be collected with permission of the user and may include prescriptions used, medical diagnosis, recent lab results, recent results of a physical examination, family medical history, electronic health records, and the like.

In some arrangements, other behavioral data may be used. For instance, whether a user has a membership to a gym, how often the user visits the gym, and the like, may be used. In some examples, global positioning system data may be used to determine or verify a position of a user (e.g., user visits a gym 5 days/week). Additionally or alternatively, detecting behaviors such as marathon running, 5K running, or the like, may be detected from sensor data, as well as time, pace, and the like. This data may be collected and used in evaluation for generating outputs.

Data associated with occupation and/or hobbies may also be considered. For instance, detection of, for instance, skydiving, as a hobby (e.g., based on altimeter sensor data from a mobile device) may indicate a risk factor for a user. In some examples, data associated with an occupation may be collected. For instance, detection of frequent changes in altitude, speed, and the like, may indicate a user is a flight attendant, pilot, or the like. This information may be used in evaluation.

In some examples, user behavior data may be collected, analyzed, and used to evaluate risk, generate outputs, provide offers, make pricing adjustments, and the like, as described herein. The collected user behavior data may further be used to identify discrepancies in information provided by the user. For example, in addition to being used to make eligibility and pricing determinations, collected user behavior data may be used to identify any discrepancies that may exist in information provided by a user, such as on an application provided by the user to the entity. For example, if a user has indicated on an application that the user is a non-smoker and user behavior data collected for the user describes or shows the user smoking, such information may be used to identify a discrepancy in the application. In such situations, the system may determine that a formal underwriting process must be undertaken or that additional information must be provided before an eligibility determination may be made.

In some examples, user data may be collected over a period of time to determine how sedentary a life a user lives. For instance, the movement of the mobile device may be tracked via one or more sensors and that information may be transmitted for processing and analysis. In some examples, this data may be collected during an eligibility evaluation process (e.g., before an output is generated, an offer is provided, or the like). Additionally or alternatively, the data may be collected during a term of, for instance, an insurance policy, to monitor a user's lifestyle. In some examples, historical data from a time prior to the user requesting a product may be collected and evaluated to identify potential risk. Data may also be collected after the user has purchased the product to continue to evaluate risk. This continuous or continued collection may be also be used for dynamic pricing (e.g., pricing that may change based on detected behaviors, such as for variable based products) and/or for renewal of a product.

As discussed herein, in some examples, a user may accept a generated output or offer and a binding agreement may be made. In some arrangements, one or more of the data collection, processing, offer and acceptance may be performed in real-time. In some examples, the binding agreement may be based solely on the data collected from interactive condition evaluation tests, the user behavior data, supplemental data, internal data, external data, and the like (e.g., without traditional underwriting, physical examination or the like). In other examples, a user may be provided with an output having a first price. Acceptance of the offer may include the user agreeing to the first price, however, an incentive may be generated for a user to provide additional information, such as recent medical examination results, lab work, or the like. Accordingly, a rebate, refund, credit, or the like, may be offered for providing this additional information.

In some examples, a user may also permit an entity to use the collected data, generated outputs, test results, and the like in determining eligibility or pricing for one or more other products. For instance, a system may generate a recommended other product (e.g., long term care insurance, auto insurance, or the like) and the data collected may be used to evaluate risk, eligibility, and the like. In some examples, the data may be used to evaluate requests made by the user for additional products.

As discussed above, biometric data such as fingerprints and the like, and/or facial recognition data may be used to authenticate a user, provide additional functionality, and the like. For instance, upon initiating an interactive condition evaluation test, a user may be requested to capture an image of himself or herself. Facial recognition may then be used to confirm that the image captured corresponds to the user. In some examples, public records may be used to confirm this information. In other examples, the user may be asked to provide an image of, for instance, a driver's license. This may then be compared to a captured image to verify the identity of the user.

In some arrangements, fingerprint or other biometric data may also be used. For instance, a user may submit a fingerprint with acceptance of an offer, for an insurance policy or the like. If a claim is then made against the policy, or a modification is requested, the user may authenticate by submitting a fingerprint.

In another example, a beneficiary of an insurance policy may be identified by his or her fingerprint. Accordingly, the beneficiary may submit the fingerprint upon a user purchasing the policy. The beneficiary may then submit a fingerprint to submit a claim.

In some arrangements, one or more aspects described herein may be embodied in an application executing on a computing device of a user. In some arrangements, upon opening the application, various functionality may be enabled. For instance, sensors may be activated, permission may be given to collect data, and the like. Although various aspects described herein are described with respect to life insurance policies, one or more aspects described herein may be used to evaluate eligibility for other products or services, such as auto insurance, homeowners insurance, long term care insurance, and the like.

One or more aspects of the disclosure may be embodied in computer-usable data or computer-executable instructions, such as in one or more program modules, executed by one or more computers or other devices to perform the operations described herein. Generally, program modules include routines, programs, objects, components, data structures, and the like that perform particular tasks or implement particular abstract data types when executed by one or more processors in a computer or other data processing device. The computer-executable instructions may be stored as computer-readable instructions on a computer-readable medium such as a hard disk, optical disk, removable storage media, solid-state memory, RAM, and the like. The functionality of the program modules may be combined or distributed as desired in various embodiments. In addition, the functionality may be embodied in whole or in part in firmware or hardware equivalents, such as integrated circuits, Application-Specific Integrated Circuits (ASICs), Field Programmable Gate Arrays (FPGA), and the like. Particular data structures may be used to more effectively implement one or more aspects of the disclosure, and such data structures are contemplated to be within the scope of computer executable instructions and computer-usable data described herein.

Various aspects described herein may be embodied as a method, an apparatus, or as one or more computer-readable media storing computer-executable instructions. Accordingly, those aspects may take the form of an entirely hardware embodiment, an entirely software embodiment, an entirely firmware embodiment, or an embodiment combining software, hardware, and firmware aspects in any combination. Furthermore, such aspects may take the form of a computer program product stored by one or more computer-readable storage media having computer-readable program code, or instructions, embodied in or on the storage media. In addition, various signals representing data or events as described herein may be transferred between a source and a destination in the form of light or electromagnetic waves traveling through signal-conducting media such as metal wires, optical fibers, or wireless transmission media (e.g., air or space). In general, the one or more computer-readable media may be and/or include one or more non-transitory computer-readable media.

As described herein, the various methods and acts may be operative across one or more computing servers and one or more networks. The functionality may be distributed in any manner, or may be located in a single computing device (e.g., a server, a client computer, and the like). For example, in alternative embodiments, one or more of the computing platforms discussed above may be combined into a single computing platform, and the various functions of each computing platform may be performed by the single computing platform. In such arrangements, any and/or all of the above-discussed communications between computing platforms may correspond to data being accessed, moved, modified, updated, and/or otherwise used by the single computing platform. Additionally or alternatively, one or more of the computing platforms discussed above may be implemented in one or more virtual machines that are provided by one or more physical computing devices. In such arrangements, the various functions of each computing platform may be performed by the one or more virtual machines, and any and/or all of the above-discussed communications between computing platforms may correspond to data being accessed, moved, modified, updated, and/or otherwise used by the one or more virtual machines.

Aspects of the disclosure have been described in terms of illustrative embodiments thereof. Numerous other embodiments, modifications, and variations within the scope and spirit of the appended claims will occur to persons of ordinary skill in the art from a review of this disclosure. For example, one or more of the steps depicted in the illustrative figures may be performed in other than the recited order, one or more steps described with respect to one figure may be used in combination with one or more steps described with respect to another figure, and/or one or more depicted steps may be optional in accordance with aspects of the disclosure.

What is claimed is:

1. A method comprising:
   receiving, by a computing device and from a first user computing device associated with a user, a request for a product;
   determining, based on the product, at least one collection procedure;
   identifying a second user computing device associated with the user;
   sending, to the second user computing device, a request to perform the at least one collection procedure, wherein the request comprises information corresponding to the at least one collection procedure;
   receiving, from the second user computing device, data collected while performing the at least one collection procedure;
   analyzing the collected data indicative of health or lifestyle of the user;
   determining, based on the health and lifestyle of the user, whether the user is eligible for a pricing adjustment of at least a component of the product; and
   outputting information indicating whether the user is eligible for the pricing adjustment.

2. The method of claim 1, wherein determining the at least one collection procedure comprises determining, based on the product, one or more types of behavior data to be collected or one or more interactive tests to be executed, and
   wherein the request to perform the at least one collection procedure comprises:
      instructions to collect the one or more types of behavior data, or
      information corresponding to the one or more interactive tests and instructions to execute the one or more interactive tests.

3. The method of claim 2, further comprising:
   prior to sending, to the second user computing device, the information corresponding to the at least one collection procedure, generating a user interface information for performing the one or more interactive tests,
   wherein sending the information comprises sending the user interface information.

4. The method of claim 1, wherein the collected data comprises one or more of: a social media post associated with the user, an email associated with the user, a text message associated with the user, a chat message associated with the user, an image associated with the user, a video associated with the user, information related to a gym membership of the user, data collected during a body measurement test, data collected during a biometric test, data collected during a mobility test, a reflex test, or data collected during a cognitive skills test.

5. The method of claim 1, further comprising:
   calculating, based on the analyzed data, one or more behavior scores for one or more types of behavior data collected during the at least one collection procedure wherein determining whether the user is eligible for the pricing adjustment comprises determining whether the one or more behavior scores meets a corresponding threshold value.

6. The method of claim 5, further comprising:
   based on a determination that the one or more behavior scores meets the corresponding threshold value:
      determining that the user is eligible for the pricing adjustment; and
      initiating the pricing adjustment of the at least a component of the product,
   wherein the information output indicates that the user is eligible for the pricing adjustment.

7. The method of claim 5, further comprising:
   based on a determination that the one or more behavior scores does not meet the corresponding threshold value, determining that eligibility of the user for the pricing adjustment is uncertain,
   wherein the information output indicates that the eligibility of the user for the pricing adjustment could not be determined and additional information is required.

8. The method of claim 1, wherein the second user computing device is different than the first user computing device.

9. A computing device comprising:
   one or more processors; and
   memory storing computer-readable instructions that, when executed by the one or more processors, cause the computing device to:
      receive, from a first user computing device associated with a user, a request for a product;
      determine, based on the product, at least one collection procedure;
      identify a second user computing device associated with the user;
      send, to the second user computing device, a request to perform the at least one collection procedure, wherein the request comprises information corresponding to the at least one collection procedure;
      receive, from the second user computing device, data collected while performing the at least one collection procedure;
      analyze the collected data indicative of health or lifestyle of the user;
      determine, based on the health and lifestyle of the user, whether the user is eligible for a pricing adjustment of at least a component of the product; and
      output information indicating whether the user is eligible for the pricing adjustment.

10. The computing device of claim 9, wherein the instructions, when executed by the one or more processors, further cause the computing device to:
    determine the at least one collection procedure by determining, based on the product, one or more types of behavior data to be collected or one or more interactive tests to be executed,
    wherein the request to perform the at least one collection procedure comprises:
       instructions to collect the one or more types of behavior data related to the user, or
       information corresponding to the one or more interactive tests and instructions to execute the one or more interactive tests.

11. The computing device of claim 10, wherein the instructions, when executed by the one or more processors, further cause the computing device to:

prior to sending, to the second user computing device, the information corresponding to the at least one collection procedure, generate user interface information for performing the one or more interactive tests; and send, to the second user computing device, the user interface.

12. The computing device of claim 9, wherein the collected data comprises one or more of: a social media post associated with the user, an email associated with the user, a text message associated with the user, a chat message associated with the user, an image associated with the user, a video associated with the user, information related to a gym membership of the user, data collected during a body measurement test, data collected during a biometric test, data collected during a mobility test, a reflex test, and data collected during a cognitive skills test.

13. The computing device of claim 9, wherein the instructions, when executed by the one or more processors, further cause the computing device to:

calculate, based on the analyzed data, one or more behavior scores for one or more types of behavior data collected during the at least one collection procedure; and determine whether the user is eligible for the pricing adjustment based on whether the one or more behavior scores meets a corresponding threshold value.

14. The computing device of claim 13, wherein the instructions, when executed by the one or more processors, further cause the computing device to:

based on a determination that the one or more behavior scores meets the corresponding threshold value:
  determine that the user is eligible for the pricing adjustment; and
  initiate the pricing adjustment of the at least a component of the product,
wherein the information output indicates that the user is eligible for the pricing adjustment.

15. The computing device of claim 13, wherein the instructions, when executed by the one or more processors, further cause the computing device to:

based on a determination that the one or more behavior scores is below the corresponding threshold value, determine that eligibility of the user for the pricing adjustment is uncertain, wherein the information output indicates that the eligibility of the user for the pricing adjustment could not be determined and additional information is required.

16. The computing device of claim 9, wherein the second user computing device comprises at least one of: a mobile computing device, a wearable device, a fitness tracker, a social networking service server, or an email server.

17. One or more non-transitory computer-readable storage media storing instructions, that when executed by a processor of a computing device, cause the computing device to:

receive, from a first user computing device associated with a user, a request for a product;

determine, based on the product, at least one collection procedure;

identify a second user computing device associated with the user;

send, to the second user computing device, a request to perform the at least one collection procedure, wherein the request comprises information corresponding to the at least one collection procedure;

receive, from the second user computing device, data collected while performing the at least one collection procedure;

analyze the collected data indicative of health or lifestyle of the user;

determine, based on the health and lifestyle of the user, whether the user is eligible for a pricing adjustment of at least a component of the product; and output information indicating whether the user is eligible for the pricing adjustment.

18. The one or more non-transitory computer-readable storage media of claim 17, wherein the instructions, when executed by the processor, further cause the computing device to:

receive, from the second user computing device, one or more types of behavior data collected while performing the at least one collection procedure, wherein the one or more types of behavior data comprise one or more of: a social media post associated with the user, an email associated with the user, a text message associated with the user, a chat message associated with the user, an image associated with the user, a video associated with the user, and information related to a gym membership of the user;

calculate, based on the analyzed data, one or more behavior scores for the one or more types of behavior data collected while performing the at least one collection procedure; and determine whether the user is eligible for the pricing adjustment based on whether the one or more behavior scores meets a corresponding threshold value.

19. The one or more non-transitory computer-readable storage media of claim 18, wherein the instructions, when executed by the processor, further cause the computing device to:

based on a determination that the one or more behavior scores meets the corresponding threshold value:
  determine that the user is eligible for the pricing adjustment; and
  initiate the pricing adjustment of the at least a component of the product,
wherein the information output indicates that the user is eligible for the pricing adjustment.

20. The one or more non-transitory computer-readable storage media of claim 18, wherein the instructions, when executed by the processor, further cause the computing device to:

based on a determination that the one or more of the one or more behavior scores is below the corresponding threshold value, determine that eligibility of the user for the pricing adjustment is uncertain, wherein the information output indicates that the eligibility of the user for the pricing adjustment could not be determined and additional information is required.

* * * * *